United States Patent [19]

Murphy

[11] Patent Number: 4,828,976

[45] Date of Patent: May 9, 1989

[54] GLUCOSE FREE MEDIA FOR STORING BLOOD PLATELETS

[75] Inventor: Scott Murphy, Ardmore, Pa.

[73] Assignee: Thomas Jefferson University, Philadelphia, Pa.

[21] Appl. No.: 905,277

[22] Filed: Sep. 9, 1986

Related U.S. Application Data

[60] Continuation-in-part of Ser. No. 730,805, May 6, 1985, abandoned, which is a continuation-in-part of Ser. No. 611,895, May 18, 1984, abandoned, and Ser. No. 667,270, Nov. 1, 1984, abandoned, which is a continuation of Ser. No. 566,709, Dec. 29, 1983, abandoned, which is a continuation-in-part of Ser. No. 550,251, Nov. 9, 1983, abandoned, said Ser. No. 611,895, is a division of Ser. No. 566,709.

[51] Int. Cl.$^4$ .................... A01N 1/02; A61K 35/14
[52] U.S. Cl. ........................................ 435/2; 424/101
[58] Field of Search ............................ 435/2; 424/101

[56] References Cited

U.S. PATENT DOCUMENTS

| | | | |
|---|---|---|---|
| 2,786,014 | 3/1957 | Tullis | 167/78 |
| 3,629,071 | 12/1971 | Sekhar | 195/1.8 |
| 3,735,005 | 5/1973 | Shio | 424/101 |
| 3,753,357 | 8/1973 | Schwartz | 62/64 |
| 3,814,687 | 6/1974 | Ellis et al. | 210/49 |
| 3,850,174 | 11/1974 | Ayres | 128/272 |
| 4,014,993 | 3/1977 | Sekhar | 424/101 |
| 4,148,879 | 4/1979 | Nelson | 424/101 |
| 4,152,208 | 5/1979 | Guirgis | 195/1.8 |
| 4,205,126 | 5/1980 | Cartaya | 435/2 |
| 4,267,269 | 5/1981 | Grode et al. | 435/2 |
| 4,269,718 | 5/1981 | Persidsky | 210/787 |
| 4,344,936 | 8/1982 | Soslau | 435/2 |
| 4,387,031 | 6/1983 | Prandi | 210/787 |
| 4,390,619 | 6/1983 | Hermening-Pittiglio | 435/2 |
| 4,405,719 | 9/1983 | Crews et al. | 424/101 |
| 4,447,415 | 5/1984 | Rock et al. | 435/2 |
| 4,695,460 | 9/1987 | Holme | 424/101 |

FOREIGN PATENT DOCUMENTS

| | | |
|---|---|---|
| 108588 | 5/1974 | European Pat. Off. . |
| 1283273 | 7/1972 | United Kingdom . |

OTHER PUBLICATIONS

Murphy et al., "Improved Storage of Platelets for Transfusion in a New Container", *Blood* 60(1): 194–200 (1982).

Simon et al., "Extension of Platelet Concentrate Storage", *Transfusion* 23(3):207–212 (1983).

Murphy, "The Preparation and Storage of Platelets for Transfusion", Mammen, Barnhart, Lusher and Walsh, PJD Publications, Ltd., Westbury, New York (1980).

Murphy, "Platelet Transfusion", *Progress in Hemostasis and Thrombosis*, vol. III, edited by Theodore H. Spaet, Grune and Stratton, Inc. (1976).

Murphy et al., "Platelet Storage at 22° C.: Role of Gas Transport Across Plastic Containers in Maintenance of Viability", Blood 46(2): 209–218 (1975).

Wice et al., "The Continuous Growth of Vertebrate Cells in the Absence of Sugar", *Journal of Biological Chemistry*, 256 (15):7812–7819 (1981).

Reitzer et al., "The Pentose Cycle" *Journal of Biological Chemistry*, 255(12):5616–5626 (1980).

Reitzer et al., "Evidence that Glutamine, Not Sugar, is the Major Energy Source for Cultured HeLa Cells", *Journal of Biological Chemistry* 254 (8):2669–2676 (1979).

Kuchler, *Biochemical Methods in Cell Culture and Virology*, Halsted Press at pp. 83, 87–88 (1977).

Kunicki et al., "A Study of Variables Affecting the Quality of Platelets Stored at 'Room Temperature'", *Transfusion* 15(5):414–421 (1975).

Holme et al., "Platelet Storage at 22° C.: Effect of Type of Agitation on Morphology, Viability and Function in Vitro", *Blood* 52(2):425–435 (1978).

Murphy et al., "Storage of Platelet Concentrates at 22° C.", *Blood* 35(4):549–557 (1970).

Tegos et al., "Platelet Glycolysis in Platelet Storage-III. The Inability of Platelets to Utilize Exogenous Citrate", *Transfusion*, 19(5):601–603 (1979).

Holme et al., *Journal of Lab. and Clin. Medicine*, 97(5):610–622 (1981), "Comparative Measurement of Platelet Size by Coulter Counter, Microscopy of Blood Smears, and Light Transmission Studies".

Abrahamsen, "A Modification of the Techniques for [51]Cr-Labelling of Blood Platelets Giving Increased Circulating Platelet Radioactivity", *Scand. J. Haemat.*, 5:53–63 (1968).

Adams, G. A. et al., "Is Plasma Really Required for Platelet Storage?", Abstract No. 628 at p. 175a Blood, Nov., 1982.

Stedman's Medical Dictionary, Williams & Wilkins, Baltimore, Md. (1982), pp. 1300–1301.

Laszlo, "Energy Metabolism of Human Leukemic Lymphocytes and Granulocytes", Blood, vol. 30, No. 2, Aug., 1967, pp. 151–167.

Murphy et al., "Platelet Size and Kinetics in Hereditary and Acquired Thrombocytopenia", New England Journal of Medicine, 286:499–504 (Mar. 9, 1972).

Osol et al., U.S. Dispensatory, 25th Ed., pp. 1194–1196 and 1270–1271, 1955.

Browdie, David et al., "Stroma-Free Hemoglobin", The American Journal of Surgery 129:365–368 (Apr. 1975).

Travenol Trade Literature for Ringer's Injection (Viaflex Brand), copyright 1977 indicating concentrations (at p. 6) of Na, K, Ca and Cl.

Travenol Trade Literature for Ringer's Injection USP (current) (listing mM and corresponding mEq/L concentrations of Na, Ca and Cl) Travenol Canada Inc.

Travenol Trade Literature Copyright 1978, 1981, 1982 and 1983, for Ringer's Injection, USP (listing concentration in mEq/L of Na, K, Ca and Cl).

Eagle, H., "Amino Acid Metabolism in Mammalian Cell Cultures", Science, 130:432–437 (1959).

Tyrode, M. V., "The Mode of Action of Some Purgative Salts", Arch. Intern. Pharmacodyn., 20:205–223 (1910).

Earle, W. R. et al., "Production of Malignancy in Vitro-IV. The Mouse Fibroblast Cultures and Changes Seen in the Living Cells", Journ. Natl. Cancer Inst., 4:165–212 (1943).

Dulbecco, R. et al., "Plaque Formation and Isolation of Pure Lines with Poliomyelitis Viruses", J. Exp. Med., 99:167–182 (1954).

Hanks, J. H. et al., "Relation of Oxygen and Temperature in the Preservation of Tissues by Refrigeration", Proc. Soc. Exp. Biol. Med., 71:196–200 (1949).

Gey, G. O. et al., "The Maintenance of Human Normal Cells and Tumor Cells in Continuous Culture", Amer. J. of Cancer, 27:45–76 (1936).

Puck, T. T. et al., "Genetics of Somatic Mammalian Cells—III. Long-Term Cultivation of Euploid Cells from Human and Animal Subjects", J. Exp. Med., 108:945–959 (1958).

Rock G. et al., "Platelet Storage: An Assessment of the Requirements for Plasma and Oxygen", Transfusion, 21(2):167–177 (1981).

Rock, G. et al., "Storage of Platelets Collected by Apheresis", Transfusion, 23(2):99–105 (1983).

Rock, G. et al., "Storage of Platelets Obtained by Apheresis Techniques", Plasma Ther. Transfrs. Technol., 3:305–308 (1982).

Wong, S. C. et al., "The Effect of Adenine on Platelet Storage", Transfusion, 22(4):283–287 (1982).

Adams, G. A. et al., "Serotonin Uptake by Stored Platelets", Thrombosis Research, 28:281–284 (1982).

Mourad, N., "A Simple Method for Obtaining Platelet Concentrates Free of Aggregates", Transfusion, 8(1):48 (Jan.–Feb. 1968).

*Primary Examiner*—Sam Rosen
*Attorney, Agent, or Firm*—Woodcock Washburn Kurtz Mackiewicz & Norris

[57] ABSTRACT

Novel methods and storage media for storing platelets in a viable condition for at least five days are disclosed. The disclosed methods comprise the steps of providing a platelet rich suspension of platelets and blood plasma; extracting supernatant plasma from that suspension to leave between about 1 to 15 mls of plasma per unit of blood platelets with those platelets to produce a concentrated platelet button; adding 40 to 70 ml/unit of a glucose free aqueous solution to said concentrated platelet button; agitating the resultant solution to resuspend the platelets to provide a synthetic suspension of those platelets; and storing that synthetic suspension in an oxygen permeable container at about 22° C., until needed for use. Two preferred glucose free aqueous platelet storage media are disclosed which generally comprise sodium citrate, sodium chloride, potassium chloride, and either sodium phosphate or calcium chloride, but not both. The subject media also optionally comprise magnesium sulfate. Results comparable to storing blood platelets in plasma are disclosed using media which free plasma for other uses and which may reduce the risk of disease transmission from platelet infusion.

43 Claims, 11 Drawing Sheets

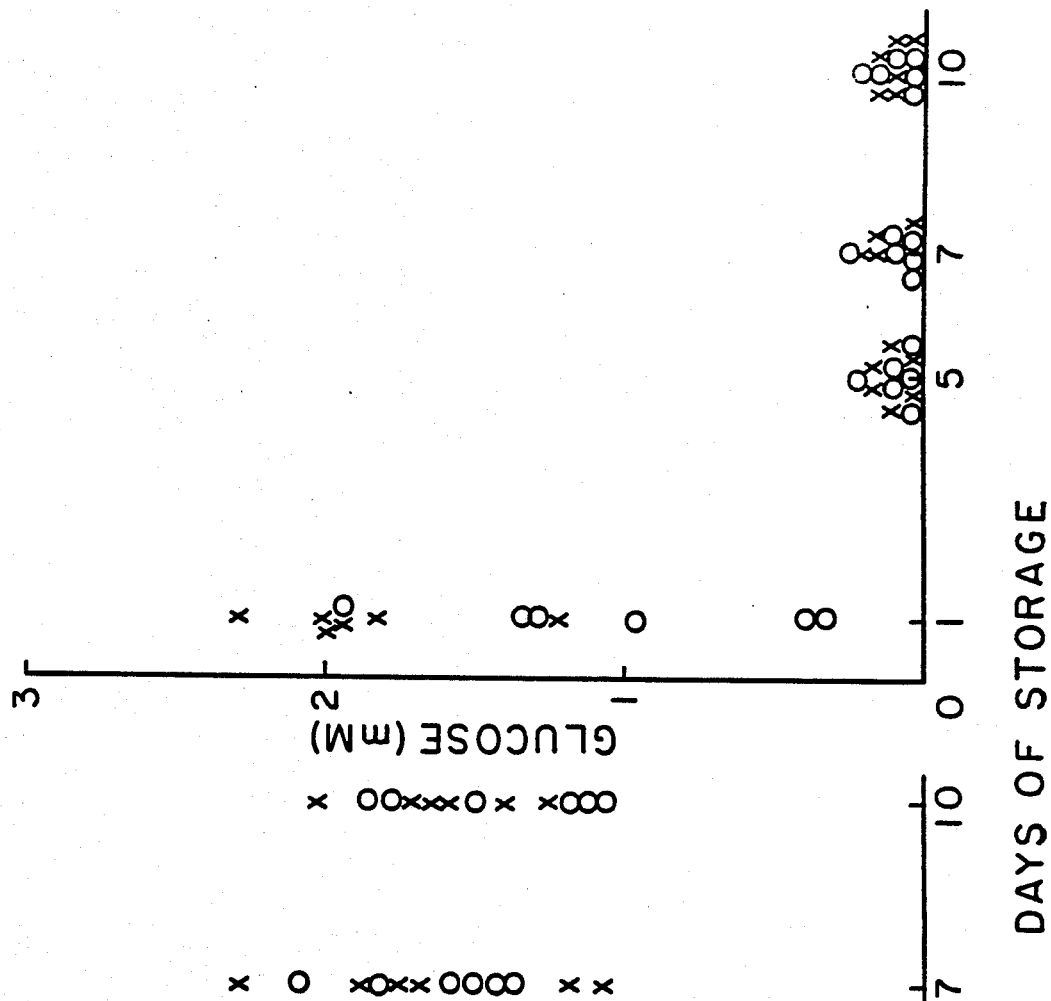

GLUCOSE FREE MEDIA FOR STORING BLOOD PLATELETS

Cross Reference to Related Applications

This application is a continuation-in-part of my prior copending application Ser. No. 730,805 filed May 6, 1985, which in turn is a continuation-in-part of my co-pending applications Ser. Nos. 611,895, filed May 18, 1984 and 667,270, filed Nov. 1,1984, which are respectively a division and a continuation of Ser. No. 566,709, filed Dec. 29, 1983, which in turn is a continuation-in-part of Ser. No. 550,251, filed Nov. 9, 1983, each of which applications is now abandoned and is hereby incorporated by reference as if fully set forth therein.

BACKGROUND OF THE INVENTION

The present invention relates to methods and media for the storage of blood platelets, and more particularly to methods and media for storing those platelets at temperatures from about 18°-30° C., preferably in the range from about 18°-30° C., preferably in the range of about 20°-24° F.. and even more preferably at about 22° C.

Platelets are obtained as a by-product from whole blood donations and from plateletpheresis procedures. Typically, they are now stored in their own plasma within a plastic container whose walls are permeable to atmospheric gases. The plasma associated with these platelets normally contains all the ingredients of normal plasma, plus citrate, which is added as an anti-coagulant, and dextrose at 5 times the physiologic level. The increased dextrose is added for the benefit of red cells which require it during storage, and is generally accepted to be required for platelet storage as well.

In routine blood banking practice, donations of a unit of blood (450 ml into 67.5 anti-coagulant) are processed by centrifugation into three fractions—red cells, plasma, and platelets. The volume of packed red cells from a unit is approximately 180 ml with a remaining volume of plasma and anti-coagulant of about 337.5 ml. As used in the remainder of this application, the term "plasma" includes any anti-coagulant which has been added thereto at the time of its initial collection. The red cells (referred to as packed red cells) are typically suspended in approximately 47.5 ml of plasma. Platelets are suspended in approximately 50 ml of plasma. This platelet containing product is typically referred to as platelet concentrate. The remaining 240 ml of plasma is frozen as fresh frozen plasma.

Recent advances have allowed blood banks to store platelet concentrates at 22° C. for five days. See Murphy et al, "Improved Storage of Platelets for Transfusion in a New Container", Blood 60(1):194-200 (1982); Simon et al, "Extension of Platelet Concentrate Storage", Transfusion, 23(3):207-212 (1983). The extended storage of platelets at 22° C. provides the flexibility to allow inventory planning so that platelets can be available at widely dispersed sites when needed. However, the above described storage procedure requires that platelets be suspended in 50 ml plasma which is then infused into the patient along with the platelets.

There are disadvantages to storing platelets in large volumes of plasma which are then infused into a recipient. Diseases may be transmitted by plasma infusion. It is certain that hepitatis-B and nonA, nonB-hepitatis may be transmitted by such plasma infusions. It has also now been reported that the newly recognized acquired immunodeficiency syndrome (AIDS) may be transmitted through plasma infusion. Patients may also exhibit allergic reactions to plasma which are at least annoying, and occasionally fatal. Furthermore, plasma is valuable because it can be fractionated into its components such as albumin and coagulation factors for treatment of specific patients. A milliliter of plasma is worth at least about 4-5 cents. Therefore, the plasma used to suspend platelets is worth as much as $2.50 per unit. Since 4 million units of platelets are administered yearly in the United States, the use of plasma as a storage medium for platelets may waste up to $10 million annually of plasma. Furthermore, the use of platelets in the United States has been increasing as a general trend.

A great deal is known about human platelet cells. General papers describing techniques, materials and methods for storage of blood platelets are described by Murphy et al. in "Improved Storage of Platelets for Transfusion in a New Container", Blood 60(1), July, 1982; by Murphy in "The Preparation and Storage of Platelets for Transfusion", Mammer, Barnhart, Lusher and Walsh, PJD PUblications Ltd., Westbury, N.Y. (1980); by Murphy in "Platelet Transfusion", Progress in Hemostasis and Thrombosis, Vol. III, Edited by Theodore H. Spaet, Grune and Stratton, Inc. (1976); and by Murphy et al. in "Platelet Storage at 22° C.: Role of Gas Transport Across Plastic Containers in Maintenance of Viability", Blood 46(2):209-218 (1975) each of which publications is hereby incorporated by referenceaas if fully set forth herein.

There are, of course, many culture media and/or physiologic solutions which are deemed acceptable for use in maintaining and/or culturing vertebrate cells. Such solutions include Earle's solution (a tissue culture medium); Fonio's solution (used for stained smears of blood platelets); Gey's solution (for culturing animal cells); Hank's solution (for culturing animal cells); Heyem's solution (a blood diluent used prior to counting red blood cells); Krebs-Ringers solution (a modification of Ringers solution prepared by mixing NaCl, KCl, $CaCl_2$, $MgSO_4$, and phosphate buffer, pH 7.4); lactated Ringers solution (containing NaCl, sodium lactate, $CaCl_2$ (dihydrate) and KCl in distilled water); Locke's solution (for culturing animal cells); Locke-Ringers solution (containing NaCl, $CaCl_2$, KCl, $MgCl_2$, $NaHCO_3$, glucose and water); Ringers solution (resembling blood serum and its salt constituents, containing 8.6 grams of NaCl, 0.3 gms of KCl and 0.33 gms of CaCl in each thousand milliliters of distilled water, used typically for burns and wounds or used in combination with naturally occurring body substances, e.g., blood serum, tissue abstracts and/or more complex chemically defined nuclear solutions for culturing animal cells); and Tyrode's solution (a modified Locke's solution). See Stedman's Medical Dictionary, pp. 1300-1301, Williams and Wilkins, Baltimore, Md. (1982).

The maintenance and/or culturing of live vertebrate cells creates different problems depending upon the particular type of cells employed. It is known, for example, that blood cells, such as platelets, have many metabolic properties similar to those of certain other types of cells. In Blood 30:151 (1967), for example, it is suggested that the metabolic properties of blood cells are similar in some respects to those of tumor cells. On the other hand, there exists a considerable body of prior art directed specifically to the problem of storing stable suspensions of blood cells, such as blood platelets. Prior work on the storage of blood platelets, has shown that the duration of platelet storage is limited by the continuing production of lactic acid from dextrose by the platelets. Although this provides energy for the platelets, the lactic acid acidifies the medium, which acidity eventually destroys the platelets. It has also been shown that platelets consume oxygen during storage for energy production, the end product of which process is a gas, $CO_2$ which, unlike lactic acid, can leave the container through the plastic walls in which it is normally stored. The production of $CO_2$ does not acidify the storage medium for these platelets. In addition to the glycolysis of dextrose, fatty acids and amino acids typically present in the plasma may be used as substrates for oxidative metabolism of stored platelet cells.

Various techniques are disclosed in the patent literature relating to the fractionation of blood into useful end products. In British Patent No. 1,283,273, a method and apparatus for separating plasma from whole blood to produce a plasma end product is disclosed wherein the remaining blood fractions are returned to a donor. In U.S. Pat. No. 4,269,718 (Persidsky) a method of centrifugal separation of platelets from blood using saline as a washing and displacing solution is disclosed. In Prandi, U.S. Pat. No. 4,387,031, a composition is disclosed for separating erythrocytes and plasma in blood.

The patent literature also discloses various preservative or culture media which are disclosed as being useful in conjunction with the storage of platelets. In U.S. Pat. No. 4,390,619 (Harmening-Pittiglio) an ion-exchange resin for slow release of phosphate buffer is disclosed. This patent contains an extensive discussion of oxidative phosphorylation and glycolysis mechanisms of platelets, and the relationship thereof to platelet storage. In U.S. Pat. No. 2,786,014 (Tullis) and U.S. Pat. No. 3,629,071 (Sekhar) various glucose and electrolyte containing platelet storage media are disclosed which are intended for use in the storage of platelets at temperatures in the range of 4°–5° C. Similarly, U.S. Pat. No. 4,152,,208 discloses a method and medium for storing stabilized leucocytes which are disclosed as being stored at temperatures from about 4° C. to about 30° C., which are kept in a basic salt solution or a minimum essential medium which sustains the viability of the leucocytes in the blood. In U.S. Pat. No. 4,267,269 (Grode et al.) a red cell storage solution is disclosed containing adenine, glucose or fructose, sodium chloride and mannitol. U.S. Pat. No. 3,814,687 (Ellis et al.), U.S. Pat. No. 3,850,174 (Ayes) and the aforementioned British No. 1,283,273 patent generally relate to the separation of formed elements from plasma in blood fractionation processes. In U.S. Pat. No. 4,152,208 (Guirgis) a variety of leucocyte preservative solutions and the use of such solutions in blood fractionation procedures is disclosed, including Eagles' MEM (columns 3 and 4) containing inter alia, glutamine, leucine, isoleucine, phenylalanine, tyrosine, phosphates and sodium and potassium chlorides, for use in conjunction with anticoagulants such as sodium citrate. See also U.S. Pat. No. 4,205,126 (Cartaya). U.S. Pat. No. 3,753,357 (Schwartz) broadly disclosed various preservative or culture media useful in conjunction with the storage of blood cells.

In "Platelet Size and Kinetics in Hereditary and Acquired Thrombocytopenia" by Murphy et al., New England Journal of Medicine 286: 499–504 (Mar. 9, 1972), a method is disclosed for determining platelet volume wherein blood samples are drawn, mixed with acid-citrate-dextrose, and centrifuged to obtain platelet-rich plasma. The platelet-rich plasma is then diluted in Isoton or an isotonic buffer of sodium chloride, potassium chloride and sodium phosphate, and adjusted to a pH of 7.4 with hydrochloric acid. A Coulter counter is then used to determine platelet count and platelet volume in these samples. As disclosed at page 4 of this paper, incubation of the platelets may also be carried out with radiolabelled chromium in a Ringer-Citrate-Dextrose Solution for one hour, in accordance with the technique of Abrahamsen.

In Abrahamsen, "A Modification of the Technique for $^{51}$Cr-Labeling of Blood Platelets Giving Increased Circulating Platelet Radioactivity", *Scand. J. Haemat.* 5:53–63 (1968) the influence of temperature, pH, incubation medium and inoculation time on the uptake of radiolabelled chromium by platelets is discussed. As disclosed at page 54 of this reference, in vitro studies were conducted on platelets which were separated from platelet-rich ACD-plasma (obtained from whole blood donations) by centrifugation. Different samples of these platelets were resuspended in equal volumes of incubation media and "left for half an hour at the temperature selected for the experiment". Among the media tested were saline-citrate-dextrose, Ringers-citrate-dextrose and Ringers-citrate. Identical amounts of radiochromium were then added to these suspensions and incubation continued until it was stopped after various periods of time by adding ascorbic acid. See FIG. 1 at page 55 of Abrahamsen. In vivo studies were also conducted wherein ACD-platelets were incubated at 20 ml. of Ringers-Citrate-Dextrose Solution for various periods of time at the temperature and with the concentration of radiocromium for the selected experiment. In these in vivo studies, samples of the incubated platelets were reinfused into the patient, and recovered to determine, for example, platelet half-lifetime.

In addition to these studies, Abrahamsen reports his concern that certain factors which increase platelet uptake of radiochromium "might induce irreversible platelet damage with reduced recovery and shortening of platelet survival." Abrahamsen reports that platelet recovery and survival time were evaluated using various incubation procedures in Ringers-Citrate-Dextrose which were compared with the results after incubation in ACD plasma in the same subject. Abrahamsen reports:

Platelet recovery and survival were not affected when platelets were incubated in Ringer-Citrate-Dextrose for one-half, one and two hours . . . or after increasing chromate dosage."

Abrahamsen concludes:

"According to these findings, incubation in Ringer-Citrate at room temperatures seems preferable. Even a platelet uptake of $^{51}$CR after incubation for one hour or less is nearly identical in saline and Ringer-Citrate-Dextrose is preferred as incubation medium." See Abrahamsen at page 59.

In addition to the above, please refer to U.S. Pat. No. 4,447,415 (Rock et al.) and to Adams GA et al. "Is Plasma Really Required for Platelet Storage? ", Abstract No. 628 at page 175a *Blood,* Nov., 1982.

As discussed hereinafter, one of the preferred embodiments of the present invention utilizes a synthetic platelet storage medium to which glutamine has been added. Although not related to the storage or culturing of blood cells, the following publications do disclose that glutamine may be a substrate for oxidative phosphorylation in a certain type of cancer cells, namely, HeLa cells. See "The Continuous Growth of Vertebrate Cells in the Absence of Sugar" by Wice et al., *Journal of Biological Chemistry*, 256(15): 7812–7819 (1981); "The Pentose Cycle", by Reitzer et al., *Journal of Biological Chemistry*, 255(12): 5616–5626 (1980); and "Evidence that Glutamine, Not Sugar is the Major Energy Source for Cultured HeLa Cells", by Reitzer et al., *Journal of Biological Chemistry*, 254(8):2669–2676 (1979). See also Kuchler, Biochemical Methods in Cell Culture and Virology, Halsted Press at page 83, 87–88, (1977).

Notwithstanding the considerable work conducted in this area, a need still exists for a simple safe, inexpensive method for storing human blood platelets in viable condition while increasing the amount of blood plasma which is freed for other uses.

SUMMARY OF THE INVENTION

The present invention provides novel methods and storage media for storing platelets in a viable condition for three to seven days, preferably at least about five days, at temperatures from about 18°–30° C., especially from about 20°–24° C. and preferably at about 22° C. The methods of the present invention comprise the steps of providing a platelet rich suspension of platelets in blood plasma; extracting supernatant plasma from that suspension to leave between about 1 to 15 mls of plasma per unit of blood platelets with those platelets to produce a concentrated platelet button; adding 40–70 ml/unit of a glucose free aqueous solution to said concentrated platelet button; agitating the resultant solution to resuspend the platelets to provide a synthetic suspension of those platelets; and storing that synthetic suspension in an oxygen permeable container at about 22° C. until needed for use.

The present invention provides two preferred alternate aqueous platelet storage media. The first of these (referred to herein as PSM-1) consists essentially of sodium citrate, sodium chloride, sodium phosphate and potassium chloride, and is essentially free of glucose, calcium and magnesium. The second of these media (referred to herein as PSM-2) consists essentially of sodium citrate, sodium chloride, potassium chloride, magnesium sulfate and calcium chloride and is essentially free of glucose and phosphate. The aforementioned storage media are preferred because they produce results comparable to storage in plasma over periods of up to ten days and do not present the commercial manufacturing problems which may be encountered in attempting to sterilize glucose free storage media comprising glucose and/or both phosphate and calcium/magnesium.

When 55 mls per unit of either PSM-1 or PSM-2 is used to store one unit of platelets and not more than 15 mls. of associated plasma in an oxygen permeable container maintained at 22° C., pH will remain in excess of 6.2, preferably in excess of 6.6, during a 10 day storage period. pH (measured at 22° C.) is more stable in the PSM-1 medium (containing sodium phosphate) because of the buffering action of that phosphate.

A preferred alternate blood platelet storage medium further comprises a platelet permeable non-glycolytic substrate for oxidative phosphorylation, such as glutamine. Alternate substrates includes oxaloacetate, malate, fumarate, succinate, alpha-ketogluterate, oxalosuccinate, isocitrate, cis-aconitate, and/or an amino acid which may be transformed to such citric acid cycle intermediates such as glutamic or aspartic acids. Further alternate substrates include amino acids and fatty acids which give rise to acetyl-CoA, including leucine, isoleucine, phenylalanine, tyrosine, acetoacetic acid, acetone, and those fatty acids which may be metabolized by beta-oxidation. Particularly preferred at the present time is the addition of glutamine as a substrate for oxidative phosphorylation. It has been found that the addition of glutamine as a substrate for oxidative phosphorylation may extend the active metabolism of stored platelets to thereby extend their viability for seven days or longer.

Accordingly, a primary object of the present invention is the provision of a novel method of processing and storing human blood platelets.

A further object of the present invention is the provision of a novel platelet storage medium which will free substantial amounts of natural plasma for other uses.

These and further objects of the present invention will become apparent from the following more detailed description.

BRIEF DESCRIPTION OF THE DRAWINGS

FIG. 2 is a graph of lactate concentrations (in mM) versus days of storage showing lactate concentrations of test of platelets stored in the PSM-1 and PSM-2 media of FIG. 1;

FIG. 3 is a graph of glucose concentrations (in mM) versus days of storage for the PSM-1 (open circles) and PSM-2 (X's) platelet storage media of FIG. 1;

DESCRIPTION OF THE PREFERRED EMBODIMENTS

Figure 1:
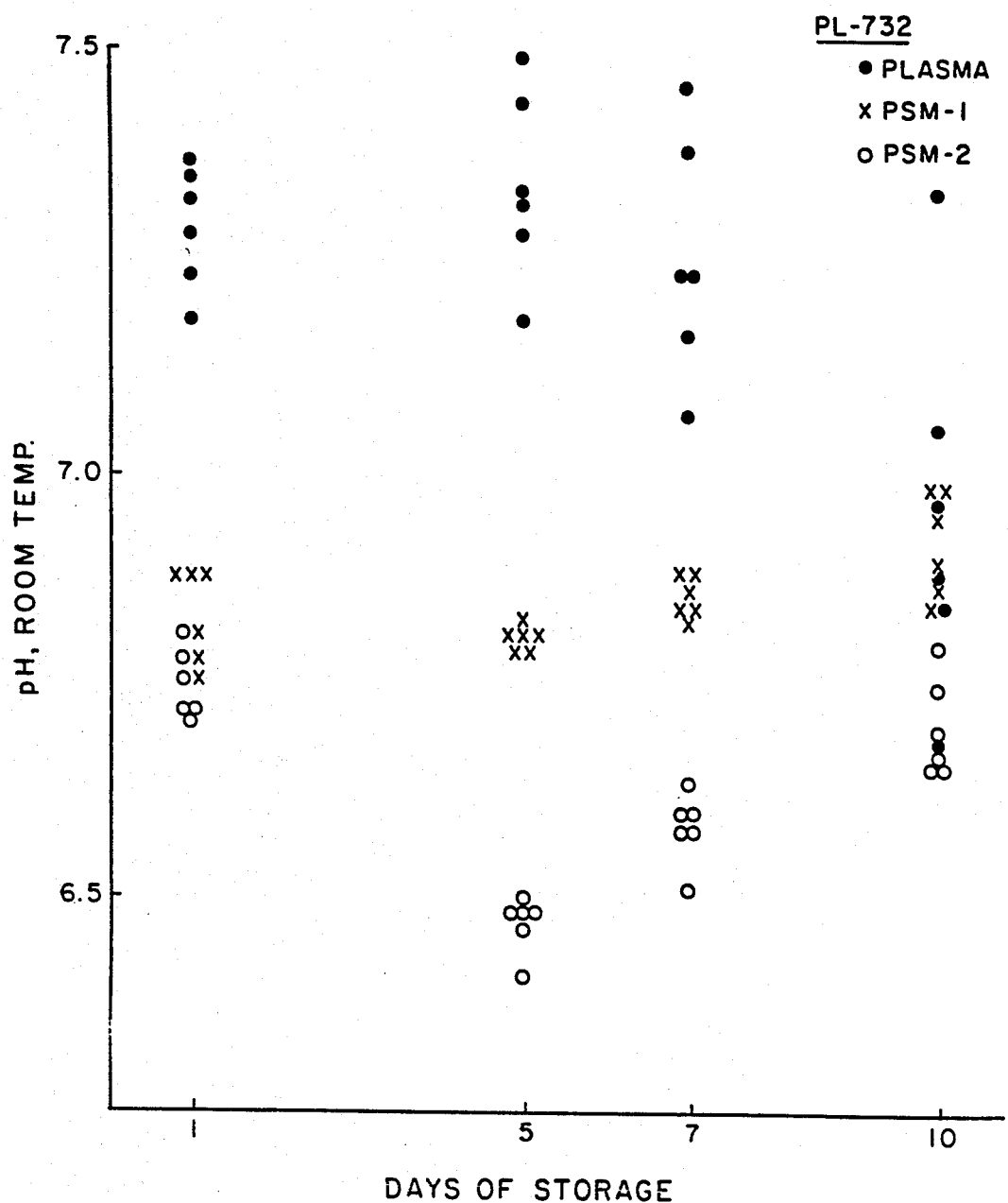
FIG. 1 is a graph plotting the pH over a ten day storage period for tests of platelets stored in plasma (solid circles), PSM-1 (X's) or PSM-2 (open circles)

A primary object of the present invention is the provision of a disease free artificial storage medium for platelets which will permit storage for at least five days preferably 7 days, most preferably 10 days, at a temperature of from about 18°–30° C., preferably at about 20°–24° C. and most preferably at about 22° C. At the end of the storage, the platelets should be viable. By that it is meant that a majority of the stored platelets will circulate normally after infusion into a recipient. Several studies indicate that platelet viability is correlated to maintenance of normal platelet morphology. See Murphy et al., "Improved Storage of Platelets for Transfusion in a New Container", *Blood* 60(1):194–200 (1982); Kunicki et al., "A Study of Variables Affecting the Quality of Platelets Stored at 'Room Temperature'", *Transfusion*, 15(5):414–421 (1975); and Holme et al., "Platelet Storage at 22° C.: Effect of Type of Agitation on Morphology, Viability, and Function in Vitro", *Blood* 52(2):425–435, (1978). As their name implies, platelets circulate as thin, compact disks with few processes. In most situations, loss of viability correlates with sphering, swelling and pseudopod formation. In the subsequently described experiments, platelet morphology has been used as one index of viability. This has been accomplished through the use of conventional phase microscopy. Additionally, the extent of platelet shape change in response to thrombin and the dispersion of size distribution by Coulter counter have been objectively measured. As reported in the above-mentioned Murphy et al. and Holme et al. papers, it has been shown that these measures correlate with microscopic morphology and in vivo viability.

In order to maintain viability, the cell must generate new adenosine triphosphate (ATP) continuously to meet its energy needs. Two pathways are normally available-glycolysis and oxidative phosphorylation. In glycolysis, one molecule of glucose is converted to two molecules of lactic acid to generate two molecules of ATP. In oxidation, glucose, fatty acid, or amino acid enters the citric acid cycle and is converted to carbon dioxide ($CO_2$) and water. This pathway requires the presence of an adequate supply of oxygen. It is a much more efficient system than glycolysis. For example, oxidative metabolism of glucose to $CO_2$ and water yields 36 molecules of ATP.

It has been recognized that blood platelets will meet their energy needs in a manner which is not necessarily consistent with their long-term storage in a viable condition. When given adequate oxygen, platelets produce most of their ATP through oxidation, but continue to produce lactic acid instead of diverting all metabolized glucose through the oxidative pathway. During the storage of platelets in plasma, lactic acid concentrations rise at approximately 2.5 millimolar per day. See Murphy et al., "Platelet Storage at 22° C.: Role of Gas Transport Across Plastic Containers in Maintenance of Viability", *Blood* 46(2):209–218 (1975). This leads to gradual fall in pH. As explained in the aforementioned Murphy et al. article, when lactic acid concentration rises about 20 millimolar, a pH (which started at 7.2) may reach 6.0. Since platelet viability is irreversibly lost if pH falls to 6.1 or below, a major limiting variable for platelet storage is pH. See Murphy et al., "Storage of Platelet Concentrates at 22° C.", *Blood* 35(4):549–557 (1970). At this rate of lactic acid production, pH would fall much more rapidly if it were not for naturally occurring plasma buffers, principally sodium bicarbonate.

The present invention provides a method for processing and storing human blood platelets. This method includes the steps of providing a platelet concentrate comprising blood platelets in blood plasma (including any anti-coagulant added at a time of initial blood withdrawal); extracting supernatant plasma from said concentrate to leave about 1 to 15 (preferably 4 to 15) milliliters of plasma per unit of blood platelets to produce a platelet button and residual associated plasma; adding 40–70, preferably 55–60, ml/unit of one of several preferred glucose free solutions to said platelet button and associated residual plasma; agitating said solution to resuspend said platelets to provide a synthetic suspension of platelets; and storing said synthetic suspension in an oxygen permeable container at a temperature from about 18°–30° C., preferably from about 20°–24° C., until needed for use.

The preferred platelet storage media comprise at least sodium, chloride, and potassium and are essentially free of glucose. They further comprise either calcium or phosphate, but not both. If calcium is present, the medium further comprises an amount of citrate sufficient to prevent platelet clumping upon resuspension of the platelet button. Magnesium is optional, but preferred when calcium is used in the medium.

One preferred platelet storage medium (PSM-1) consists essentially of an aqueous solution of 75–125, preferably 90–110, most preferably about 98 mM sodium chloride; 17–29, preferably 20–25, most preferably 23 mM sodium citrate; 19–31, preferably 22–28, most preferably about 25 mM sodium phosphate ($NaH_2PO_4$); 3–7, preferably 4–6, most preferably about 5 mM potassium chloride, and optionally 0.9–1.5, preferably 1.1–1.3, most preferably about 1.2 mM magnesium sulfate, said medium being essentially free of calcium and glucose.

A second preferred platelet storage medium, PSM-2, consists essentially of an aqueous solution of 70–120, preferably 85–105, most preferably about 95 mM sodium chloride; 17–29, preferably 20–25, most preferably about 23 mM sodium citrate; 3–7 preferably 4–6, most preferably about 5 mM potassium chloride, 0.9–1.5 preferably 1.1–1.3 most preferably about 1.2 magnesium sulfate; and 1.9–3.1, preferably 2.2–2.8, most preferably about 2.5 mM calcium chloride, said medium being essentially free of glucose and phosphate.

Those of ordinary skill in this art will recognize that each of the preferred media contain the same concentrations of sodium citrate and potassium chloride, similar concentrations of sodium chloride, optionally similar concentrations of magnesium sulfate, but quite different concentrations of sodium phosphate and calcium chloride.

Those of ordinary skill in the art will recognize that once in solution, it is the concentration of the subject ions which is important to the function of the medium, and will recognize that other compounds may be added to solution to achieve the desired mEq/L. In solution it is preferred to provide, when used, 100–300, preferably 140–240, most preferably 160–200 mEq/L sodium;

50-300, preferably 80-150, most preferably 100-125 mEq/L chloride; 0.1-100, preferably 45-75, most preferably 30-70 mEq/L citrate; and 0.1-6, preferably 1-4, most preferably about 2.4 mEq/L magnesium.

For reasons which are explained more fully hereinafter, each of the subject preferred media is essentially free of glucose. For practical considerations related in part to the tendency of calcium to precipitate in the presence of phosphate with some forms of heat sterilization, it is presently preferred to further ensure that the subject medium contains either calcium or phosphate, but not both. When calcium is used, the use of citrate concentrations effective to prevent platelet clumping upon resuspension is preferred. When a phosphate buffer is used, it is selected to be effective to maintain the pH of a unit of platelets and not more than 15 mls of associated plasma at a pH in excess of 6.6 during 7 days of storage with 55 ml-unit of said medium in an oxygen permeable container maintained at the specified temperature, preferably about 22° C. For the described media this concentration of phosphate will be 5-50, preferably 10-35, or most preferably about 25 mEq/L.

At physiologic pH, phosphate is a mixture of $H_2PO_4{-}$ and $HPO_4{-}$. Those of ordinary skill will recognize that for purposes of clarity phosphate is conveniently referred to as $H_2PO_4{-}$. As used herein, a 1 mM solution of sodium phosphate has 1 mEq/L of phosphate and 1 mEq/L of sodium. The particular sodium phosphate added to the described media is $NaH_2PO_4$.

It is not believed that this basic blood platelet storage medium provides an exogenous substrate for metabolism since it has been reported that citrate cannot enter the citric acid cycle of platelets. See Tegos et al., "Platelet Glycolysis in Platelet Storage, III. The Inability of Platelets to Utilize Exogenous Citrate", *Transfusion* 19(5):601-603 (1979). Glucose has not been incorporated into the present medium since its incorporation would result in the obligatory production of lactic acid, leading to an unacceptable lowering of pH and a loss of platelet viability. Glucose also tends to carmelize when sterilized in aqueous solutions at neutral pH.

The preferred methods of the present invention are designed to limit the amount of glucose which is available to stored platelets, and which therefore may act as a substrate for lactic acid production. The amount of glucose-containing supernatant plasma removed from the platelet concentrate, and of glucose free storage medium added to the blood platelets and residual associated plasma ensure that the concentration of glucose in the resulting synthetic suspension is less than about 10 mM/L at the onset of storage. Preferably, the extraction and storage medium addition procedures are performed such that the concentration of glucose in the resulting suspension is about 5 mM/L, typically about 3 mM/L, at the onset of storage. As explained hereinafter, this concentration of glucose permits glycolysis to proceed until about a 1.5 mM or less concentration has been obtained, which occurs after about three days storage using the preferred methods and media of the present invention.

In order to maintain the pH of the resultant synthetic suspension of platelets at an acceptable level, the aforementioned medium has also been formulated such that pH at the onset of storage is in excess of 6.5, preferably between about 6.6 and 7.0.

As mentioned above, the preferred PSM-1 solution maintains the pH of the suspension above 6.5, preferably between 6.6-7.0 during up to 10 days of storage. This is accomplished using a phosphate buffer, preferably sodium phosphate, which is added in the aforementioned concentrations. As demonstrated hereinafter, this buffering is sufficient to accommodate the lactic acid derived from metabolism of platelet glycogen as well as the residual plasma glucose not removed during concentrate preparation.

Optionally an additional platelet permeable, non-glycolytic substrate for oxidative phosphorylation may be added to the synthetic platelet suspension prior to storage. Glutamine is the preferred non-glycolytic substrate for oxidative phosphorylation. In a preferred embodiment, glutamine may be incorporated as a component in the platelet storage medium in a concentration of between 5 to 25 preferably about 20 mM/L. Alternatively, other non-glycolytic substrates for oxidative phosphorylation may be selected from the group consisting of oxaloacetate, malate, fumarate, succinate, alpha-ketogluterate, oxalosuccinate, isocitrate, cis-aconitate, glutamine, amino acid precursors of citric acid cycle intermediates, amino and/or fatty acids precursors of acetyl-CoA, and mixtures thereof. Such amino acid precursors of citric acid cycle intermediates include those selected from the group consisting of glutamic acid, aspartic acid, and mixtures thereof. Such precursors of acetyl-CoA may be selected from the group consisting of leucine, isoleucine, phenylalanine, tyrosine, acetoacetic acid, acetone, fatty acids metabolized by beta-oxidation and mixtures thereof. It is also presently preferred to add magnesium to the subject storage medium, particularly when calcium is present, since this element is important to proper cell function.

The present invention may be understood further from the following examples:

Platelet rich-plasma (PRP) and platelet concentrates (PC) were prepared from whole blood donations anticoagulated with citrate-phosphate-dextrose (CPD) or acid-citrate-dextrose, as described in *Blood* 52(2): 425-435, except that the supernatant plasma was extracted from the bag containing the platelet button as completely as possible using a Fenwal plasma extractor (Fenwal Laboratories, Deerfield, Ill.). The residual amount of plasma ranged from 4 to 15 ml. 45 ml of Ringers solution (Travenol Laboratories, Deerfield, Ill.) and 15 ml of 2.5% sodium citrate solution were added to the bag containing the platelet button. The bag was left undisturbed for 45 minutes before being placed on a platelet agitator (Helmer Labs., St. Paul, Minn.) for resuspension. It is preferred to perform such an incubation step for at least 30 minutes prior to agitating of the solution to resuspend the platelets. After two hours of agitation, the platelets were completely resuspended. The PC was then transferred to a PL/732 container (Fenwal, Inc.). This container is known to provide adequate oxygen supply. See *Blood*, 60(1): 194-200 (1982). Various supplements to be tested were then added to the container which was stored on the platelet agitator at 22° C. The final media were tested (concentrations indicated refer to final concentrations):

1. Ringers and citrate only: Ri-Ci (Sodium, 175 mM; potassium, 3 mM; calcium, 3.4 mM; chloride, 117 mM; citrate, 21 mM).
2. Ringers-citrate and phosphate: Ri-Ci-Pho ($HPO_4$, 8 mM).
3. Ringers-citrate, phosphate and glutamine: Ri-Ci-Pho-Glut (L-glutamine) (GIBCO Labs, Grand Island, N.Y.), 20 mM).

4. Ringers-citrate, phosphate and glucose: Ri-Ci-Pho-Gluc (glucose, 25 mM).
5. Plasma control. Some PC were resuspended in plasma in the usual fashion for comparative purposes.

Platelet count, mean platelet volume, and the dispersion (geometric standard deviation) of the size distribution were determined using a Coulter counter.

$pO_2$ and pH were determined as previously described using a pH/blood gas analyzer. The oxygen consumption rate, $C(O_2)$, (nmoles/min/10 plts) was determined by a steady state technique:

$$C(O_2) = \frac{KO_2 (148-pO_2)}{\text{platelet content} \times 10^9}$$

$KO_2$ is the capacity of the container for $O_2$ transport (nmoles/min/atm). The equation above states that the oxygen consumption of the platelets inside the container is equal to the flux of oxygen through the walls of the container.

Lactate and glucose concentrations were determined as previously described. (See *Blood* 46 (2):209–218 (1975)). Extent of platelet shape change with thrombin (IU per ml final conc.) was measured using a Payton aggregometer. It was quantitated by the ratio of extinction $E_{1200}^1/E_{1200}$ where $E_{1200}$ represents the extinction of the platelets before addition of thrombin and $E_{1200}^1$, the extinction after. See Holme, et al., *Journal of Lab. and Clin. Medicine*, 97(5):610–622 (1981).

3 ml. samples of PC to be studied were taken at day 1, 3, 5 and 7. The final volumes of PC at day 7 ranged from 51–58 ml.

In this test a decrease in pH levels below 6.2 was observed when platelets were stored in the basic Ringers-citrate medium, Ri-Ci. Addition of sodium phosphate, Ri-Ci-Pho, prevented most of this fall in pH. Addition of glutamine, Ri-Ci-Pho-Glut, did not alter the serial pH measurements observed with Ri-Ci-Pho. However, the buffering capacity of the phosphate was not sufficient to maintain pH if glucose was added in the medium, Ri-Ci-Pho-Gluc. The presence of glucose caused additional lactic acid accumulation overcoming the buffering capacity of Ri-Ci-Pho. These pH results are set forth in Table I:

TABLE I

| | pH | | | | |
|---|---|---|---|---|---|
| | Days of Storage | | | | |
| | 0 | 1 | 3 | 5 | 7 |
| 1. Ri—Ci[4]* | 6.77 ± 0.04* | 6.65 ± 0.08 | 6.37 ± 0.09 | 6.16 ± 0.29 | N.D. |
| 2. Ri—Ci—Pho[10] | 7.16 ± 0.07 | 6.78 ± 0.16 | 6.70 ± 0.17 | 6.79 ± 0.12 | 6.84 ± 0.11 |
| 3. Ri—Ci—Pho—Glut[8] | 7.30 ± 0.10 | 6.86 ± 0.19 | 6.70 ± 0.11 | 6.70 ± 0.23 | 6.77 ± 0.20 |
| 4. Ri—Ci—Pho—Gluc[1] | 7.26 | 6.96 | 6.42 | 6.16 | 5.90 |
| 5. Plasma[4] | 6.92 ± 0.06 | 7.21 ± 0.07 | 7.33 ± 0.08 | 7.21 ± 0.09 | 7.00 ± 0.19 |

*In this and other tables ± refers to ±1.
S.D. and the number of studies is in the parentheses.

The following table confirms that lactic acid production increased when glucose was added to the Ri-Ci solution:

TABLE II

| | LACTATE (mM) | | | | |
|---|---|---|---|---|---|
| | Days of Storage | | | | |
| | 0 | 1 | 3 | 5 | 7 |
| 1. Ri—Ci[4] | 0.9 ± 0.7 | 1.7 ± 0.6 | 3.9 ± 0.9 | 6.5 ± 3.6 | N.D. |
| 3. Ri—Ci—Pho Glut[4] | 0.9 ± 0.3 | 3.9 ± 2.2 | 5.9 ± 1.1 | 6.4 ± 0.9 | 6.2 ± 1.1 |
| 4. Ri—Ci—Pho Gluc[1] | 1.0 | N.D. | 7.7 | 9.0 | N.D. |
| 5. Plasma[5] | 0.9 ± 0.4 | 2.9 ± 1.6 | 5.4 ± 1.9 | 10.1 ± 1.8 | N.D. |

Table III shows glucose concentrations under these storage conditions. It is apparent that glucose conmsumption and lactate production continue as long as glucose is present at the concentration above 1.5 mM. Such lactate production exceeds buffering capacity. In Ri-Ci-Pho-Glut, lactate production ceases on day 3 because substrate has been exhausted. These results also substantiate the fact that, if glucose is present, the rates of lactate production in artificial media and in plasma are similar.

TABLE III

| | GLUCOSE (mM) | | | | |
|---|---|---|---|---|---|
| | Days of Storage | | | | |
| | 0 | 1 | 3 | 5 | 7 |
| 1. Ri—Ci[4] | 4.8 ± 1.9 | 4.2 ± 1.8 | 2.6 ± 1.8 | 1.6 ± 0.5 | N.D. |
| 3. Ri—Ci—Pho—Glut[4] | 5.0 ± 0.6 | 3.5 ± 1.7 | 1.5 ± 0.2 | 1.5 ± 0.2 | 1.4 ± 0.2 |
| 4. Ri—Ci—Pho—Gluc[1] | 27.0 | N.D. | 22.0 | 19.8 | N.D. |
| 5. Plasma[5] | 21.7 ± 1.1 | 21.1 ± 1.6 | 18.6 ± 1.6 | 17.8 ± 1.6 | N.D. |

Table IV demonstrates that there was some decrease in oxygen consumption during storage, however, this decrease was not related to the absence of glucose or plasma in the medium since it also took place with platelets stored in plasma. The results in Ri-Ci-Pho-Glut firmly establish that oxygen consumption continues from day 3 to day 7 when glucose is not being consumed.

TABLE IV $C(O_2)$ (nmoles/min/$10^9$ plts)

| | Days of Storage | | | |
|---|---|---|---|---|
| | 1 | 3 | 5 | 7 |
| 1. Ri—Ci[4] | 1.55 ± 0.41 | 1.01 ± 0.22 | 0.87 ± 0.23 | N.D. |
| 2. Ri—Ci—Pho[6] | 1.67 ± 0.24 | 1.46 ± 0.59 | 1.06 ± 0.43 | 0.58 ± 0.22 |
| 3. Ri—Ci—Pho—Glut[8] | 1.59 ± 0.30 | 1.47 ± 0.20 | 1.20 ± 0.30 | 0.76 ± 0.34 |
| 5. Plasma[4] | 2.00 ± | 1.47 ± | 1.13 ± | 0.91 ± |

TABLE IV-continued

| C($O_2$) (nmoles/min/$10^9$ plts) | | | |
|---|---|---|---|
| Days of Storage | | | |
| 1 | 3 | 5 | 7 |
| 0.34 | 0.59 | 0.08 | 0.08 |

The morphology of the platelets when stored in the Rigners-citrate medium with addition of phosphate and glutamine was well preserved at days 3 and 5. Some platelet clumping was apparent at day 5. This was reflected in a 10% decrease in platelet count at that time (Table V). This phenomenon progressed as storage continued beyond 5 days. A 10% fall in platelet count was also observed when platelets were stored in plasma.

TABLE V

PLATELET COUNT (% of Day 1 Value) (Coulter Counter)

| | Days of Storage | | | |
|---|---|---|---|---|
| | 1 | 3 | 5 | 7 |
| 1. Ri—Ci[4] | 100 | 95 ± 5 | 89 ± 3 | 85 ± 14 |
| 2. Ri—Ci Pho[6] | 100 | 93 ± 9 | 79 ± 13 | 64 ± 13 |
| 3. Ri—Ci—Pho—Glut[8] | 100 | 94 ± 7 | 89 ± 9 | 73 ± 14 |
| 4. Plasma[4] | 100 | 95 ± 3 | 90 ± 4 | 91 ± 7 |

Using phase microscopy it was apparent that platelets stored in the Ringers-citrate medium with phosphate and glutamine were mostly discoid and had intact internal structure at days 3 and 5. The percentage of swollen platelets with internal disintegration (balloon forms) was in the range, 5-10%, at 5 days of storage. These subjective impressions were reflected in objective measurements of the extends of platelet shape change (VI) and dispersion of Coulter size distribution (Table VII).

TABLE VI

EXTENT OF SHAPE CHANGE, ($E_{1200l}/E_{1200}$)

| | Days of Storage | | | |
|---|---|---|---|---|
| | 1 | 3 | 5 | 7 |
| 1. Ri—Ci[4] | 1.21 ± 0.05 | 1.11 ± 0.03 | 1.04 ± 0.05 | N.D. |
| 2. Ri—Ci—Pho[5] | 1.14 ± 0.01 | 1.10 ± 0.02 | 1.08 ± 0.03 | 1.06 ± 0.02 |
| 3. Ri—Ci—Pho—Glut[8] | 1.14 ± 0.02 | 1.10 ± 0.02 | 1.07 ± 0.03 | 1.06 ± 0.02 |
| 4. Plasma[4] | 1.21 ± | 1.10 ± | 1.13 ± | 1.09 ± |

TABLE VI-continued

EXTENT OF SHAPE CHANGE, ($E_{1200l}/E_{1200}$)

| Days of Storage | | | |
|---|---|---|---|
| 1 | 3 | 5 | 7 |
| 0.07 | 0.03 | 0.05 | 0.03 |

TABLE VII

SIZE DISPERSION (COULTER COUNTER)

| | Days of Storage | | | |
|---|---|---|---|---|
| | 1 | 3 | 5 | 7 |
| 1. Ri—Ci[4] | 1.83 ± 0.08 | 1.92 ± 0.15 | 2.05 ± 0.46 | 2.18 ± 0.25 |
| 2. Ri—Ci—Pho[6] | 1.81 ± 0.04 | 1.82 ± 0.08 | 2.02 ± 0.19 | 2.15 ± 0.16 |
| 3. Ri—Ci—Pho Glut[8] | 1.82 ± 0.07 | 1.85 ± 0.07 | 1.95 ± 0.16 | 2.07 ± 0.09 |
| 5. Plasma[4] | 1.81 ± 0.04 | 1.85 ± 0.09 | 1.87 ± 0.08 | 1.98 ± 0.08 |

In previous studies, the maintenance of in vivo viability has been observed when dispersion is below 2.0 and when extent of shape change is above 1 08. See Blood 60(1): 194–200 and Blood 52(2): 425–435. In the present experiments the dispersion measurements were below 2.0 and the extent of shape change measurements were close to 1.10 at days 3 and 5 when the platelets were stored in Ringers-citrate medium with phosphate and glutamine.

Certain of the above-identified experiments were repeated using a different batch of platelet buttons. The residual amounts of plasma in this group again ranged from 4 to 15 mls. During these tests it appeared that an error may have been made in calculating the concentration of phosphate used in the previous tests.

The following tests were conducted as described above, except that each sample was observed either on the seventh or eighth day. As seen from the following data, these studies confirm the previous results. It should be noted that during this particular series of tests, the pH using a Ringers-citrate medium was not observed to fall below 6.2, but rather to about 6.5, and then to rise in subsequent observations. Nonetheless, these studies confirm the desirability of using an addition of phosphate to the Ringers-citrate solution to maintain the pH of the medium substantially above those values, and further confirm that with the addition of glucose, with or without phosphate, pH falls to unacceptably low values.

TABLE VIII

| | pH | | | | | | | |
|---|---|---|---|---|---|---|---|---|
| | Days of Storage | | | | | | | |
| | 0 | 1 | 3 | 5 | 6 | 7 | 8 |
| Ri→Ci[4] | 6.94 ± 0.06[4] | 6.69 ± 0.07[4] | 6.51 ± 0.06[3] | 6.53 ± 0.05[3] | 6.47[1] | 6.73 ± 0.04[2] | 6.66 ± 0.11[2] |
| Ri—Ci—Pho[5] | 7.17 ± 0.11[3] | 6.82 ± 0.04[4] | 6.64 ± 0.11[5] | 6.79 ± 0.08[4] | 6.63[1] | 6.91 ± 0.06[4] | |
| Ri—Ci—Gluc[5] | 6.93 ± 0.05[5] | 6.70 ± 0.06[5] | 6.35 ± 0.08[5] | 5.77 ± 0.14[5] | | 5.61 ± 0.06[5] | |
| Ri—Ci—Pho—Gluc[6] | 7.27 ± 0.05[6] | 6.85 ± 0.07[4] | 6.61 ± 0.12[4] | 6.47 ± 0[2] | 5.75 ± 0.24[4] | 6.01 ± 0.12[2] | 5.51 ± 0.08[4] |

TABLE IX

| | LACTATE (mM) | | | | | | | |
|---|---|---|---|---|---|---|---|---|
| | Days of Storage | | | | | | | |
| | 0 | 1 | 3 | 5 | 6 | 7 | 8 |
| Ri—Ci[4] | 0.84 ± 0.27[4] | 1.95 ± 0.51[4] | 4.54 ± 1.22[3] | 4.81 ± 0.22[3] | | 3.84 ± 0.12[3] | 4.28[1] |
| Ri—Ci—Pho[5] | 1.29 ± 0.70[3] | 3.09 ± 0.42[3] | 5.94 ± 0.69[4] | 5.27 ± 1.22[4] | 1.15[1] | 4.36 ± 1.55[4] | |
| Ri—Ci—Gluc[5] | 0.92 ± 0.27[5] | 2.54 ± 0.36[5] | 6.30 ± 0.68[5] | 13.65 ± 2.00[5] | | 16.31 ± 1.03[5] | |
| Ri—Ci—Pho— | 1.15 ± 0.29[6] | 3.32 ± 0.67[4] | 7.16 ± 0.75[4] | 10.18 ± 0.54[2] | 17.64 ± 3.60[4] | 15.97 ± 2.66[2] | 20.20 ± 0.7[4] |

TABLE IX-continued

| | LACTATE (mM) | | | | | | |
|---|---|---|---|---|---|---|---|
| | Days of Storage | | | | | | |
| | 0 | 1 | 3 | 5 | 6 | 7 | 8 |
| Gluc[6] | | | | | | | |

TABLE X

| | GLUCOSE (mM) | | | | | | |
|---|---|---|---|---|---|---|---|
| | Days of Storage | | | | | | |
| | 0 | 1 | 3 | 5 | 6 | 7 | 8 |
| Ri—Ci[4] | 2.82 ± 0.35[4] | 2.42 ± 0.37[4] | 0.51 ± 0.55[3] | 0.04 ± 0.07[3] | 0[1] | 0.07 ± 0.10[2] | 0[2] |
| Ri—Ci—Pho[5] | 3.48 ± 0.88[3] | 1.96 ± 0.77[4] | 0.43 ± 0.61[5] | 0.03 ± 0.05[4] | 0.10[1] | 0.03 ± 0.05[4] | |
| Ri—Ci—Gluc[5] | 23.04 ± 1.15[5] | 22.60 ± 0.98[5] | 20.27 ± 1.27[5] | 16.46 ± 1.34[5] | | 14.89 ± 1.44[5] | |
| Ri—Ci—Pho—Gluc[6] | 22.10 ± 1.43[6] | 20.98 ± 1.64[4] | 18.85 ± 1.28[4] | 18.07 ± 0.60[2] | 13.11 ± 2.48[4] | 15.07 ± 0.17[2] | 11.24 ± 1.50[4] |

TABLE XI

| | $C(O_2)$ (nmoles/min/$10^9$ plts) | | | | | | |
|---|---|---|---|---|---|---|---|
| | Days of Storage | | | | | | |
| | 0 | 1 | 3 | 5 | 6 | 7 | 8 |
| Ri—Ci[4] | 0.99 ± 0.19[4] | 0.88 ± 0.23[3] | 0.78 ± 0.19[3] | 0.71[1] | 0.62 ± 0.14[2] | 0.62 ± 0.08[2] | |
| Ri—Ci—Pho[5] | 1.01 ± 0.31[4] | 0.83 ± 0.25[5] | 0.85 ± 0.35[4] | 0.47[1] | 0.64 ± 0.19[4] | | |
| Ri—Ci—Gluc[5] | 0.70 ± 0.13[5] | 0.67 ± 0.27[5] | 0.54 ± 0.24[5] | | 0.11 ± 0.08[5] | | |
| Ri—Ci—Pho—Gluc[6] | 0.78 ± 0.10[4] | 0.66 ± 0.10[4] | 0.67 ± 0.10[2] | 0.19 ± 0.14[4] | 0.47 ± 0.27[2] | 0.02 ± 0.0[4] | |

TABLE XII

| | PLATELET COUNT PER $mm^3$ | | | | | | |
|---|---|---|---|---|---|---|---|
| | Days of Storage | | | | | | |
| | 0 | 1 | 3 | 5 | 6 | 7 | 8 |
| Ri—Ci[4] | | 1,095,600.00 ± 314,341.88[4] | 1,073,200.00 ± 323,489.92[3] | 1,197,500.00 ± 163,897.86[3] | 717,600[1] | 1,047,400.00 ± 119,254.18[3] | 717,600[1] |
| Ri—Ci—Pho[5] | | 1,579,275.00 ± 590,865.59[4] | 1,590,225.00 ± 584,842.31[4] | 1,294,975.00 ± 499,736.27[4] | 1,977,300.00[1] | 1,156,800.00 ± 377,997.38[4] | |
| Ri—Ci—Gluc[5] | | 1,452,180.00 ± 269,785.80[5] | 1,460,400.00 ± 270,425.58[5] | 1,432,080.00 ± 293,690.70[5] | | 1,462,290.00 ± 300,746.57[5] | |
| Ri—Ci—Pho—Gluc[6] | | 1,395,150 ± 35,700.00[4] | 1,199,250.00 ± 232,266.72[4] | 1,006,200.00 ± 160,796.08[2] | 1,377,300.00 ± 37,707.82[4] | 931,950.00 ± 97,368.60[2] | 1,392,600.00 ± 33,313.06[4] |

TABLE XIII

| | EXTENT OF SHAPE CHANGE ($E_{1200}l/E_{1200}$) | | | | | | |
|---|---|---|---|---|---|---|---|
| | Days of Storage | | | | | | |
| | 0 | 1 | 3 | 5 | 6 | 7 | 8 |
| Ri—Ci[4] | | 1.10 ± 0.02[4] | 1.10 + 0.02[3] | 1.07 ± 0.03[3] | 1.04[1] | 1.05 ± 0.03[2] | 1.05 ± 0.01[2] |
| Ri—Ci—Pho[5] | | 1.11 ± 0.04[4] | 1.11 ± 0.03[4] | 1.07 ± 0.02[4] | 1.10[1] | 1.06 ± 0.02[4] | |
| Ri—Ci—Gluc[5] | | 1.11 ± 0.02[5] | 1.11 ± 0.02[5] | 1.03 ± 0.02[5] | | 1.01 ± 0.01[5] | |
| Ri—Ci—Pho—Gluc[6] | | 1.13 ± 0.03[4] | 1.10 ± 0.03[4] | 1.12 ± 0.03[2] | 1.04 ± 0.04[4] | 1.07 ± 0.01[2] | 1.00 ± 0.0[4] |

TABLE XIV

| | SIZE DISPERSION (COULTER COUNTER) | | | | | | |
|---|---|---|---|---|---|---|---|
| | Days of Storage | | | | | | |
| | 0 | 1 | 3 | 5 | 6 | 7 | 8 |
| Ri—Ci[4] | | 1.81 ± 0.06[4] | 1.78 ± 0.09[3] | 1.85 ± 0.07[3] | 1.83[1] | 1.85 ± 0.07[2] | 1.96 ± 0.06[2] |
| Ri—Ci—Pho[5] | | 1.80 ± 0.13[4] | 1.76 ± 0.11[4] | 1.86 ± 0.14[3] | 1.79[1] | 1.91 ± 0.12[4] | |
| Ri—Ci—Gluc[5] | | 1.79 ± 0.03[5] | 1.77 ± 0.06[5] | 1.95 ± 0.13[5] | | 2.37 ± 0.30[5] | |
| Ri—Ci—Pho—Gluc[6] | | 1.82 ± 0.05[4] | 1.85 ± 0.06[4] | 1.90 ± 0.06[2] | 2.06 ± 0.22[4] | 1.97 ± 0.23[2] | 2.36 ± 0.2[4] |

These tests thus demonstrate that platelets can be stored for at least five days in artificial medium with maintenance of satisfactory pH, oxygen consumption, and morphology. These findings are consistent with in vivo viability and clinical efficacy as predicted through maintained morphology, see *Blood* 60(1):194-200; *Transfusion* 15(5):414-421 and *Blood* 52(2): 425-435.

The necessity of adding a buffer to the Ringers-citrate medium if pH fall is to be prevented, has been clearly demonstrated. Even in accordance with the methods of the present invention, there is always residual plasma in the concentrate. There is not sufficient buffering capacity in this residual plasma to prevent pH fall when the glucose in that plasma is converted to lactic acid, and the added citrate does not sufficiently add to the buffering capacity of the medium. Similarly, a phosphate addition is not sufficient to maintain pH if significant additions of glucose are made to the storage medium, since such additions will result in additional lactic acid production.

Glucose has therefore not been chosen as the primary substrate for platelet metabolism. Instead, the metabolic needs of each cell have been met by endogenous or exogenous amino acids or fatty acids which serve as a substrate for oxidative phosphorylation. Our findings suggest that human blood platelets may be maintained in the absence of sugar, just as Wice et al. and others have shown that certain tissue culture cells, such as HeLa cells, can be grown with glutamine as a major energy source. See Wice, et al., "The Continuous Growth of Vertebrate Cells in the Absence of Sugar", *Journal of Biological Chemistry*, 256(15): 7812–7819 (1981); and Reitzer et al., "Evidence that Glutamine, Not Sugar, is the Major Energy Source for Cultured HeLa Cells", *Journal of Biological Chemistry*, 254(8): 2669–2676 (1979).

As demonstrated above, platelets appear to be capable of sustaining oxidative metabolism even in the absence of sugar. After all glucose had been metabolized during the first three days of storage, platelets maintained morphology and continued oxygen consumption for an additional four days when glutamine or other metabolites were present to enter the citric acid cycle. It is also surprising that morphology and oxygen consumption were maintained to a considerable degree when glutamine was omitted from the Ringers-citrate-phosphate medium. If the literature reports suggesting that citrate cannot be used as an exogenous substrate are accepted, it would appear that endogenous substrates were being used by the platelets during storage. It is also probable that exogenous substrates from residual plasma are being used.

While the use of the above-mentioned phosphate buffer is preferred to prevent fall in pH, the aforementioned data suggests that platelet viability may be maintained satisfactorily during storage through the use of the above-mentioned Ringers citrate solution, particularly if pH remains above 6.0, preferably above 6.2 during a 5 to 7 day storage period. In Table A the results of 6 studies are presented in which platelet buttons were resuspended and stored, as described above, in a Ringers-citrate medium. The measured concentrations in the media for the studies were: $MgCl_2$, 1.1–1.2 mM; $CaCl_2$, 3.2–3.6 mM; KCl; 4.4–4.9 mM; NaCl, 155–182 mM; $Na_3$ Citrate, 22–24 mM. This is equivalent, in mEq/Liter to: Mg 2.2–2.4; Ca, 6.4–7.2; K, 4.4–4.9; Citrate 66–72; Na, 221–254; Cl, 168–197.

TABLE A

| | Days of Storage | | |
|---|---|---|---|
| | 1 | 5 | 7 |
| ph | 6.73 ± 0.15* | 6.55 ± 0.08 | 6.61 ± 0.13 |
| $C(O_2)$ (nmoles/min/$10^9$ plts) | 0.66 ± 0.19 | 0.52 ± 0.20 | 0.42 ± 0.19 |
| Platelet Count (% of Day 1) | 100 ± 0 | 99.5 ± 5.5 | 90.2 ± 6.1 |
| Extent of Shape Change | 1.14 ± 0.03 | 1.11 ± 0.02 | 1.09 ± 0.04 |
| Size Dispersion | 1.83 ± 0.08 | 1.82 ± 0.11 | 1.83 ± 0.11 |
| Mean Platelet Volume$^{(u3)}$ | 6.43 ± 1.05 | 7.29 ± 1.38 | 7.66 ± 1.38 |

*Mean ± 1 S.D.

To further refine the subject invention, additional tests were conducted on platelet concentrates (PC) which were prepared from platelet-rich plasma (PRP) obtained from blood donations anticoagulated with citrate-phosphate-dextrose. Platelet-depleted plasma was expressed from the container (Fenwal PL-732) with a plasma extractor and either of two platelet storage media (PSM-1 or PSM-2) was added to the platelet button. The platelets were resuspended after one hour for storage at 22 ±2° C. on a Helmer rotator (6 rotations/minute).

In vitro measurements on days 1, 5, 7, and 10 were performed using methods described above. In addition, in vivo studies were carried out by labeling stored platelets with $^{51}$ chromium and reinfusing them into the original donor. In vivo % recovery and survival T ½ (days) were calculated as described in Murphy et al., *New England Journal of Medicine* 286: 499–504 (Mar. 9, 1972), cited above.

Contents of the storage media were (mM):

TABLE B

| | PSM-1 | PSM-2 |
|---|---|---|
| Sodium citrate | 23 | 23 |
| Sodium chloride | 98 | 95 |
| Sodium phosphate ($NaH_2PO_4$) | 25 | |
| Potassium chloride | 5 | 5 |
| Magnesium sulfate | | 1.2 |
| Calcium chloride | | 2.5 |

Figure 4:
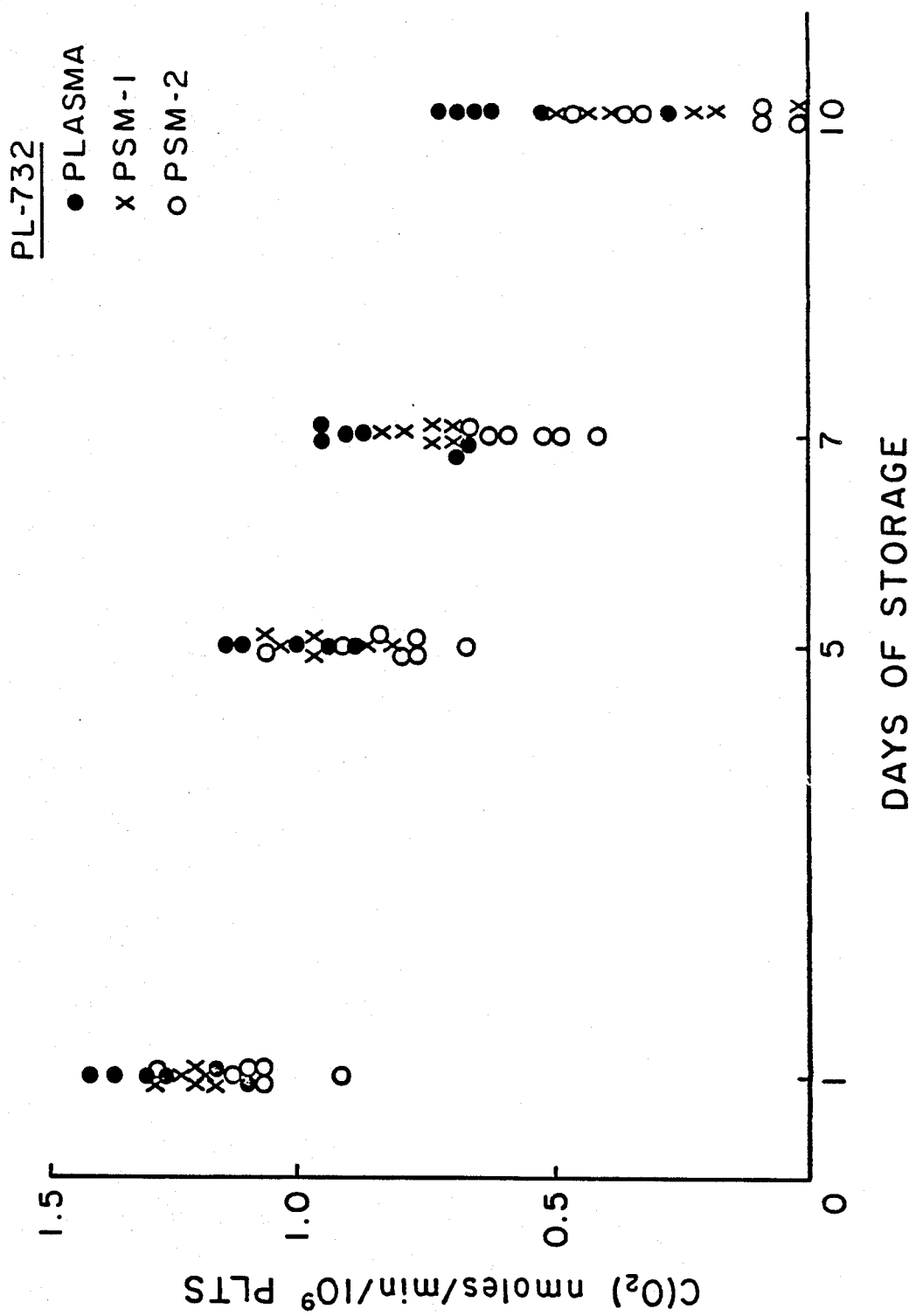
FIG. 4 is a graph of oxygen consumption, $C(O_2)$, during storage of platelets in plasma (solid circles), PSM-1 (X's) and PSM-2 (open circles) during a ten day storage period.

Referring now to the figures, FIG. 1 shows pH values during storage for PSM-1 and and PSM-2 compared to controls stored in plasma. In both media, the PC are more acid compared to plasma, but pH is well above the generally accepted lower limit of 6.0. In these experiments, pH is generally above 6.5. pH is more stable, remaining above 6.6, in PSM-1 because of the presence of the buffering phosphate. FIG. 2 shows lactate concentration during storage in the two media. FIG. 3 shows glucose concentration during storage in the two media. Glucose is present on day 1, carried over from the glucose present in the primary anti-coagulant. However, glucose is absent by day 5 and there is no further lactate production after that time. FIG. 4 shows the rate of oxygen consumption, $C(O_2)$, during storage. $C(O_2)$ continues after day 5, supporting the previous suggestion that substrates other than glucose could be used by platelets for oxidative metabolism during storage. On days 5 and 7, $C(O_2)$ appears to be greater in PSM-1 than in PSM-2.

Figure 5:
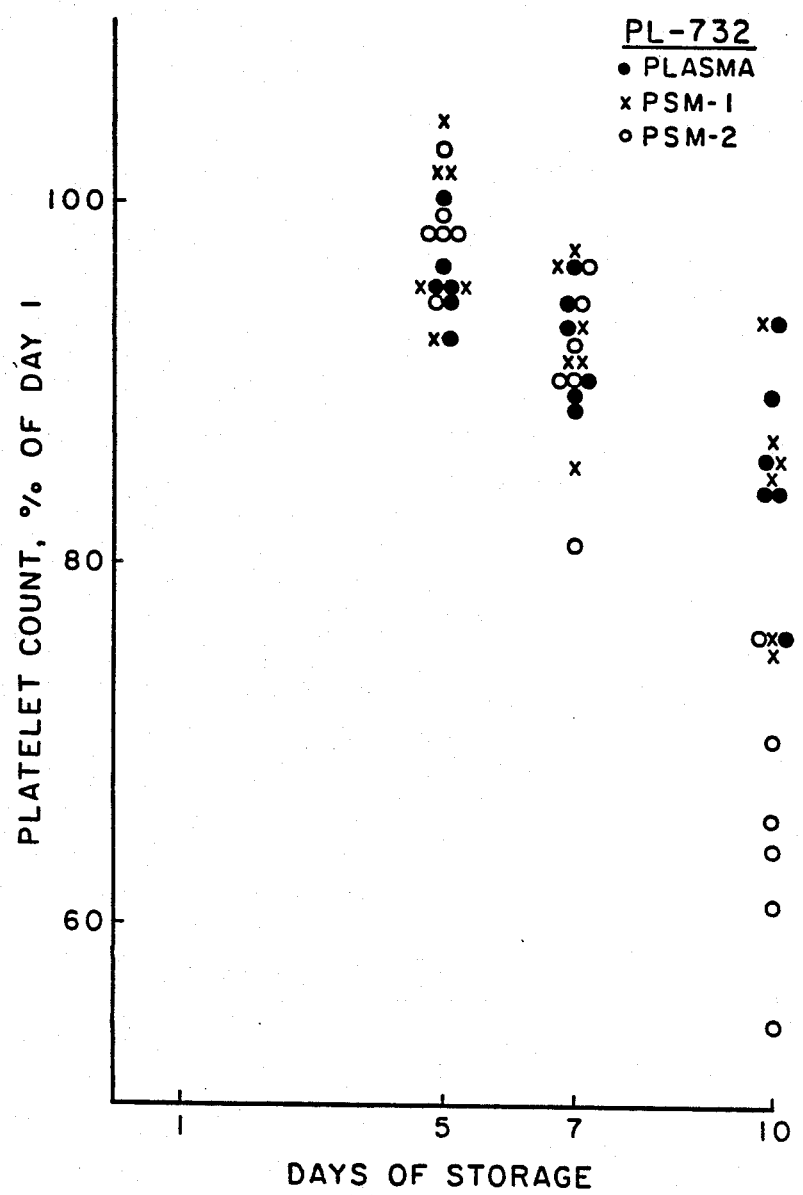
FIG. 5, is a graph of platelet count expressed as a percent of the count on day one, for days 5, 7 and 10 of storage for platelets stored in plasma (solid circles) PSM-1 (X's) and PSM-2 (open circles)

FIG. 5 shows the platelet count on days 5, 7 and 10 of storage expressed as a percent of the count on day 1. On days 5 and 7, counts in PSM-1, PSM-2, and plasma are not significantly different.

Figure 6:
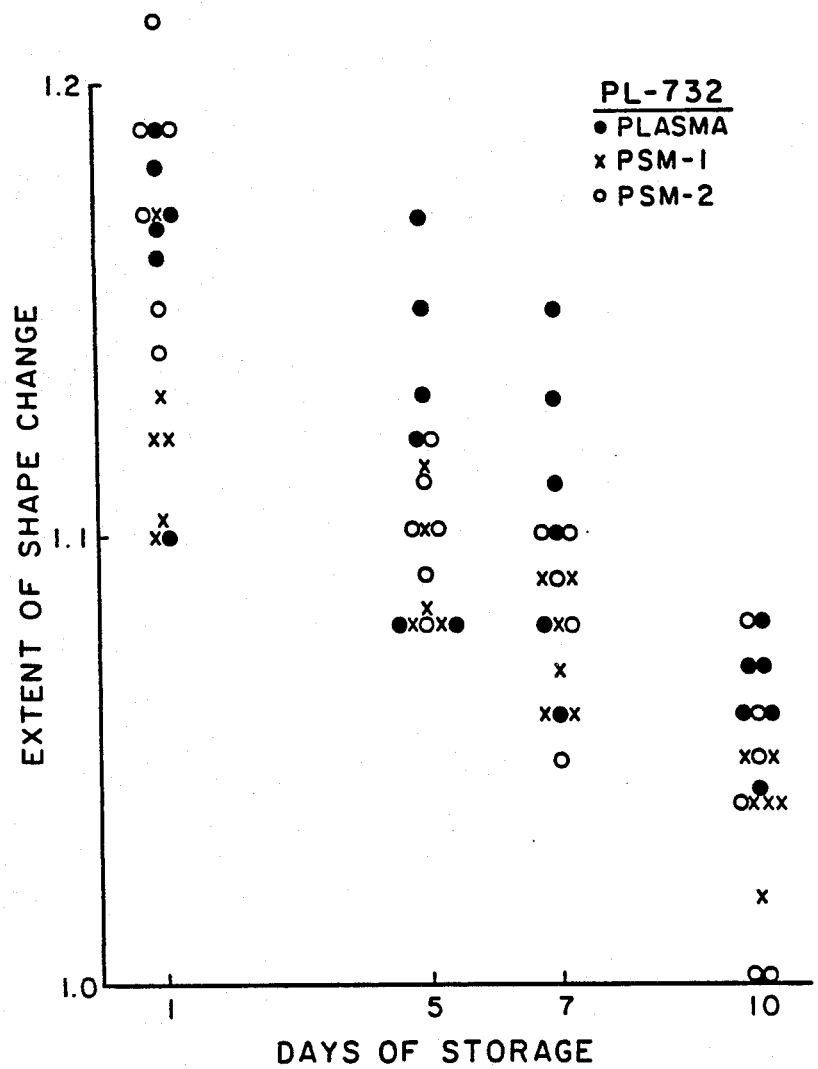
FIG. 6 is a graph showing the measurement of the extent of shape change versus days of storage for tests of platelets stored in plasma (solid circles), PSM-1 (X's) and PSM-2 (open circles)

FIG. 6 shows the measurement, extent of shape change, which reflects maintenance of disc shape. Again, on days 5 and 7 shape change responses in PSM-1, PSM-2, and plasma are not significantly different.

Figure 7:
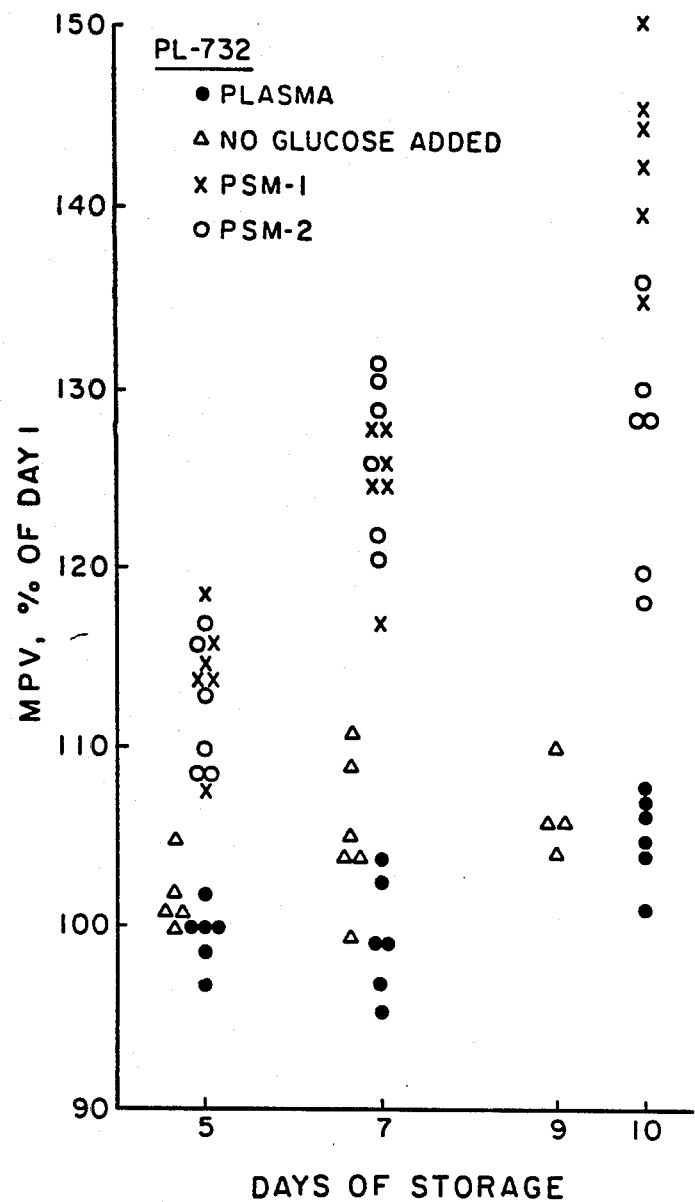
FIG. 7 is a graph showing mean platelet volume (MPV) during storage expressed as a percent of mean platelet volume on day 1 for platelets stored in plasma (solid circles), PSM-1 (X's) and PSM-2 (open circles), as well as for platelets stored in plasma obtained from blood anticoagulated with no added glucose (triangles)

FIG. 7 shows the mean platelet volume (MPV) during storage, expressed as a percent of MPV on day 1. In PSM-1 and PSM-2, there is a significant swelling during storage relative to storage in plasma. The triangles (no glucose added) show results of storage in plasma obtained from blood anticoagulated with no added glucose. Swelling is not seen under these circumstances, suggesting that swelling in PSM is not due to the absence of glucose, but rather to storage in PSM per se.

Figure 8:
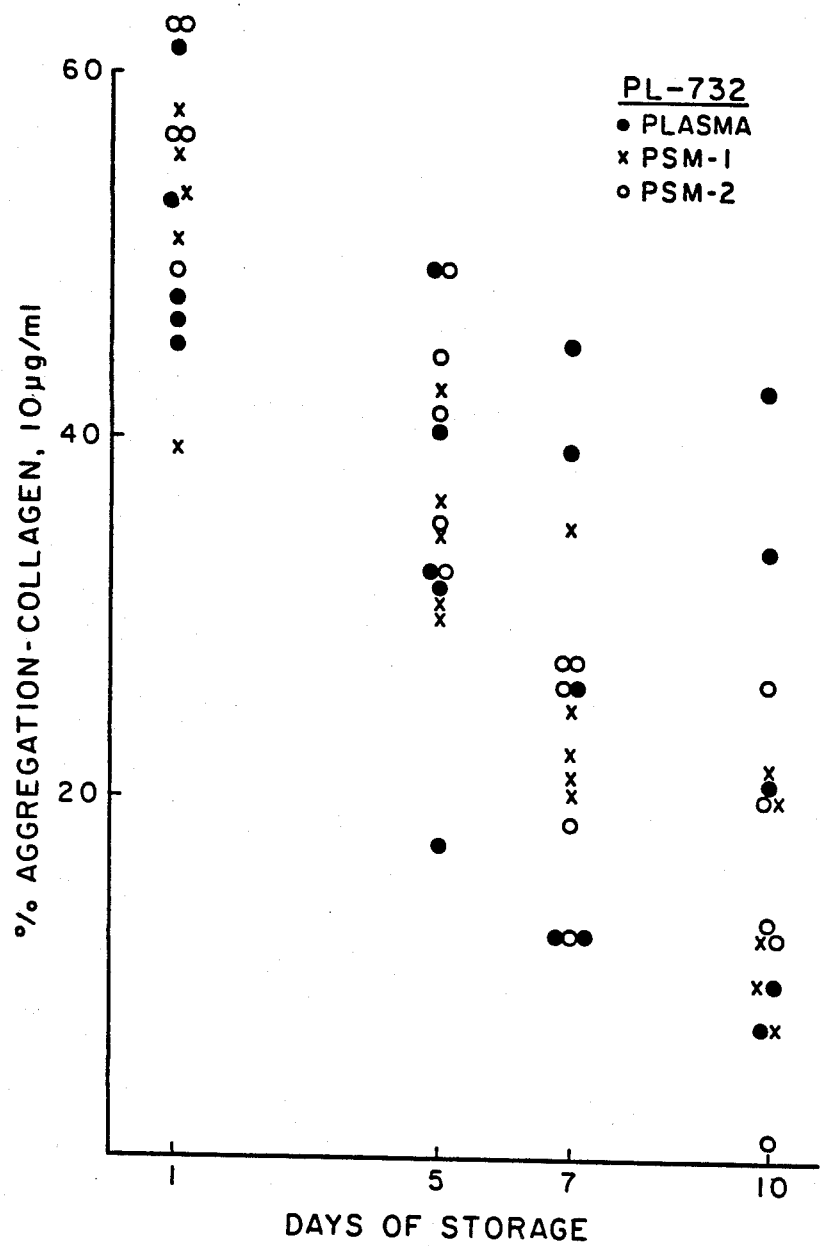
FIG. 8 is a graph of in vitro functional results in the lumiaggregometer illustrating the extent of aggregation in response to 10 ug/ml collagen for platelets stored in plasma, PSM-1 and PSM-2.
Figure 9:
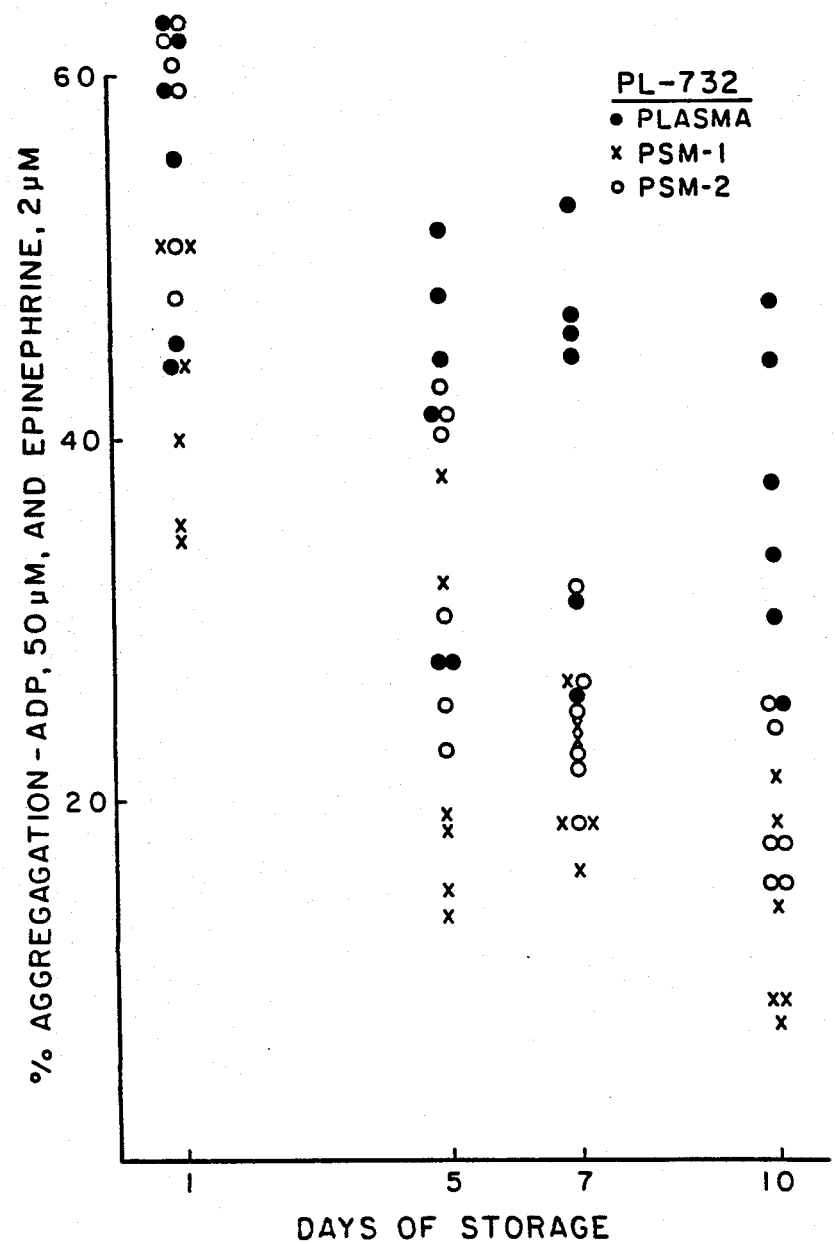
FIG. 9 is a graph similar to FIG. 8 of in vitro functional results in a lumiaggregometer showing the extent of aggregation in response to the combination of 50 μM ADP and 2μM epinephrine.
Figure 10:
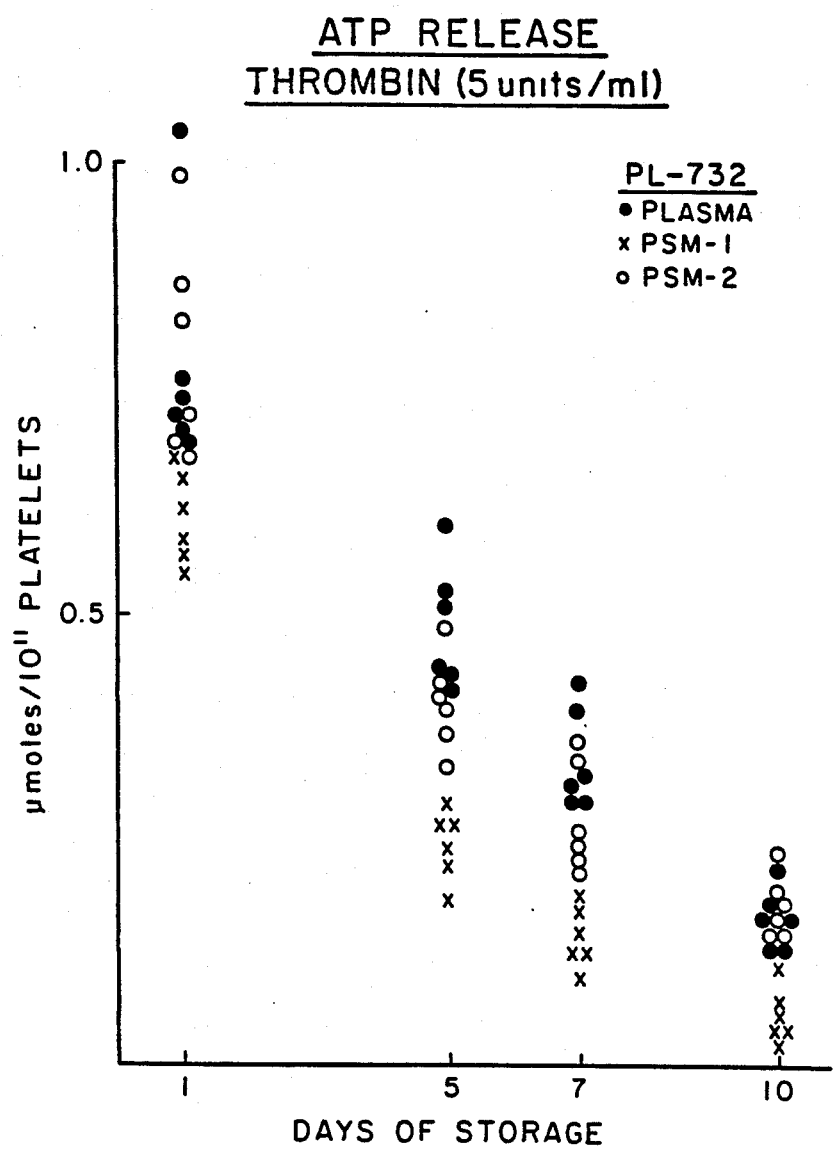
FIG. 10 is a graph similar to FIGS. 8 and 9 of in vitro functional results in a lumigggregometer showing ATP release in response to thrombin, 5 units per milliliter.

In FIGS. 8, 9 and 10 in vitro functional results in the lumiaggregometer are shown for three parameters: FIG. 8 shows the extent of aggregation in response to 10 μg/ml collagen; FIG. 9 shows the extent of aggregation in response to the combination of ADP, 50 μM and 2 μM epinephrine; and FIG. 10 shows ATP release in response to 5 units/ml. of thrombin. Generalizations from the data are that aggregation and release are only slightly reduced, if at all, with storage with PSM compared to plasma, and that ATP release is consistently better in PSM-2 compared to PSM-1.

Figure 11:
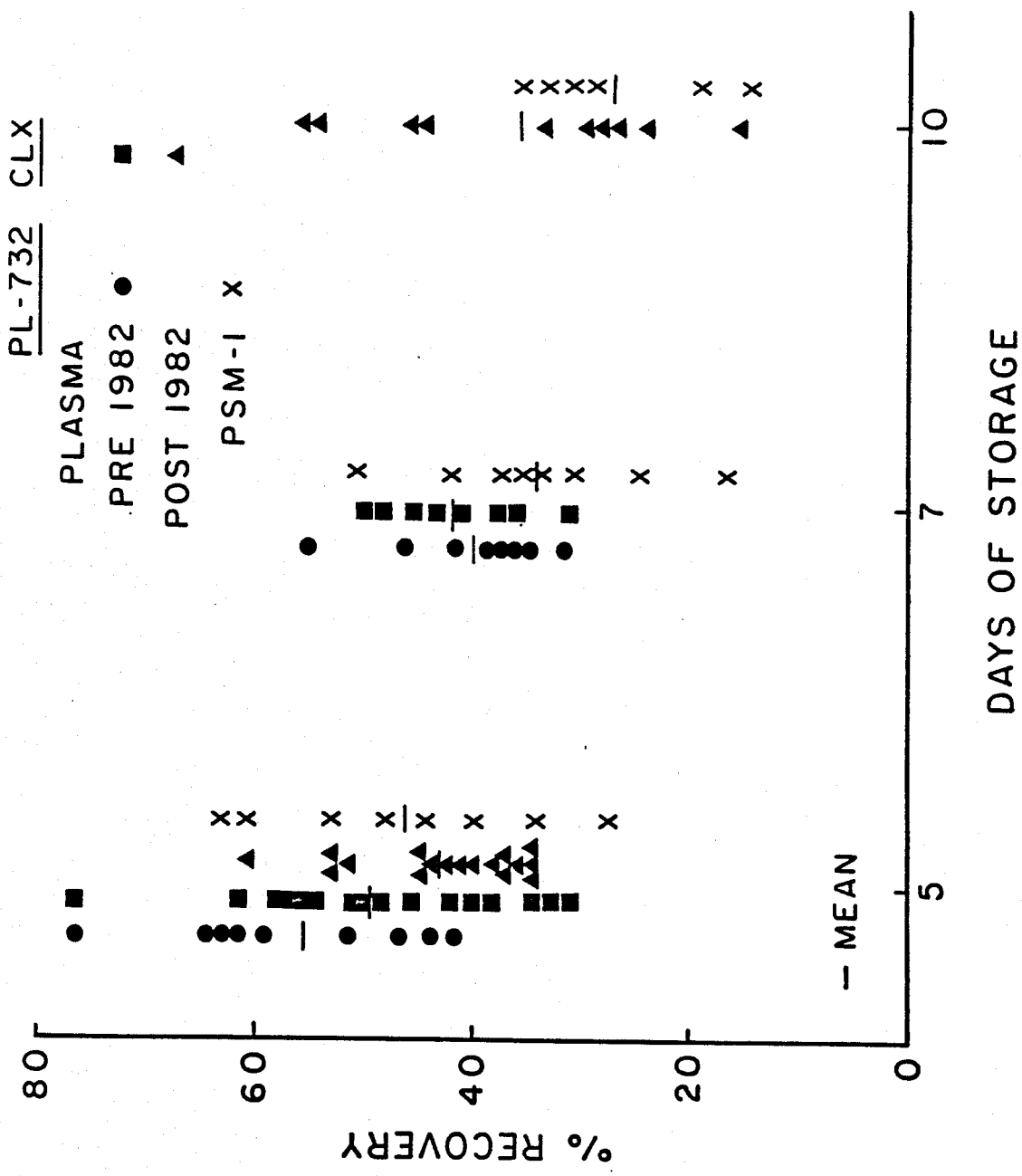
FIG. 11 is a graph of in vivo results showing percent of recovery after storage for 5, 7 and 10 days in comparison to historical controls of platelet storage in plasma —these historical controls represent storage before and after 1982 in plasma in Fenwall's PL 732 container and Cutter's CLX container, both of which are oxygen permeable containers.
Figure 12:
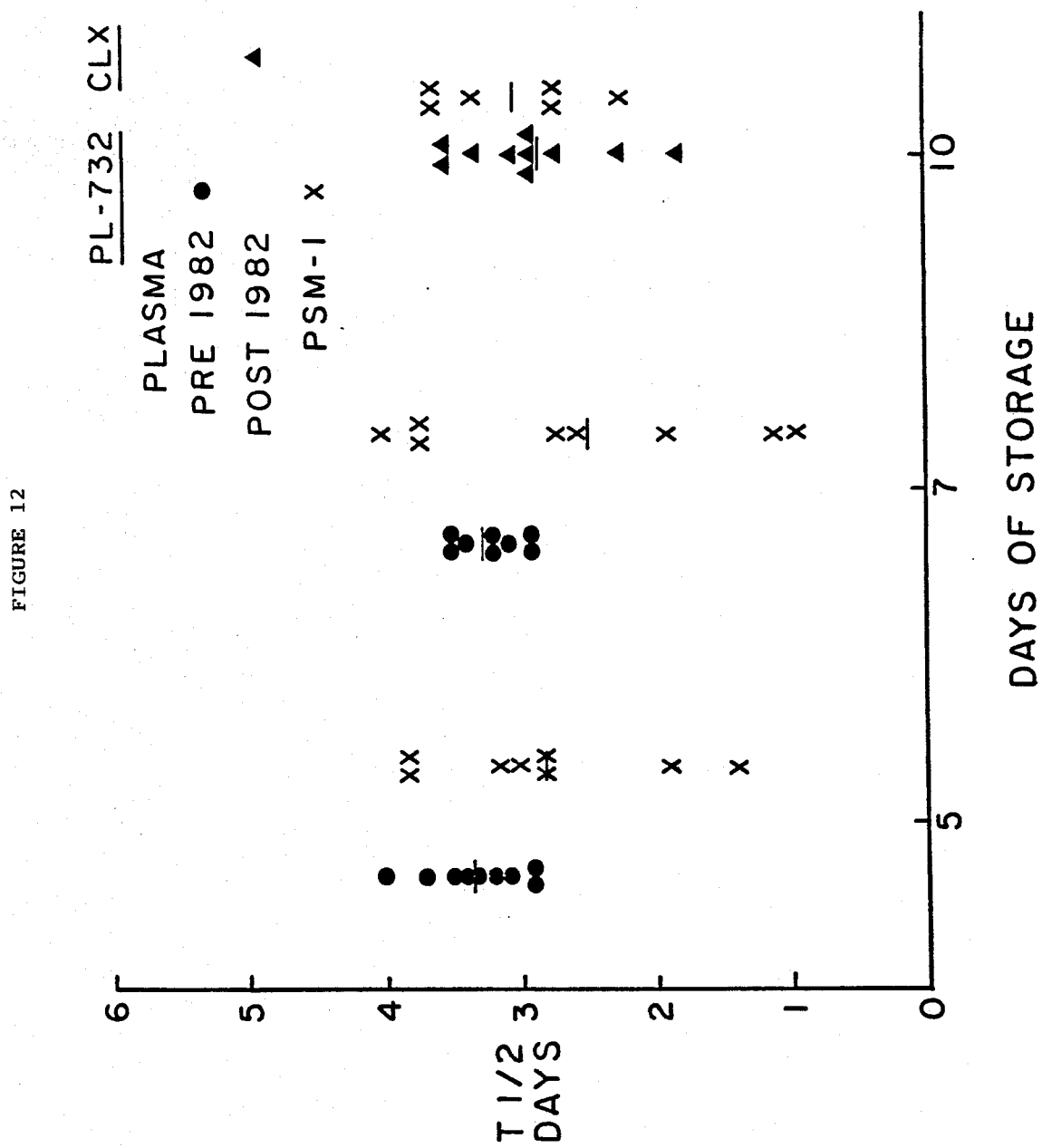
FIG. 12 is a graph comparing survival T ½ of platelets stored in PSM-1 to those stored in plasma over a 10 day storage period.

FIGS. 11 and 12 show in vivo results. Percent recovery (FIG. 11) after storage for 5, 7, and 10 days is not significantly reduced compared to historical controls of storage in plasma. The historical controls represent storage before and after 1982 in plasma in Fenwal's PL-732 container and Cutter's CLX container. Similarly, in FIG. 12, survival T ½ is not significantly different when PSM-1 is compared to plasma, although on days 5 and 7, there is somewhat more spread in the data for PSM-1.

As seen from the above, PSM-1 and PSM-2 compare quite favorably to plasma as storage media for human blood platelets. The exclusion of glucose from the subject storage media have the advantages of allowing steam sterilization at neutral pH, and preventing excessive pH fall due to lactate production. Except for an increase in mean platelet volume by day 7, PSM-1 and PSM-2 show similar in vitro and/or in vivo morphologic, metabolic, and functional parameters for storage periods of at least 7 days, and even up to 10 days, as compared to storage in plasma.

What is claimed:

1. An aqueous synthetic human blood platelet storage medium consisting essentially of:
   75–125 mM sodium chloride;
   17–29 mM sodium citrate;
   3–7 mM potassium chloride; and
   an amount of phosphate buffer which is effective to maintain a unit of platelets and not more than 15 ml of associated plasma at a pH in excess of 6.6 during seven days of storage with 55 ml per unit of said medium in an oxygen permeable container maintained at from about 20° to 24° C., said synthetic blood platelet storage medium being essentially free of glucose and calcium.

2. The storage medium of claim 1 further comprising: 0.1–1.5 mM magnesium sulfate.

3. The medium of claim 11 wherein said amount of buffer is 19–31 mM $NaH_2PO_4$.

4. The storage medium of claim 1 wherein the concentration of sodium chloride is 90–110 mM.

5. The storage medium of claim 4 wherein said sodium chloride concentration is about 98 mM.

6. The storage medium of claim 1 wherein the sodium citrate concentration is 20–25 mM.

7. The storage medium of claim 6 wherein the concentration of sodium citrate is about 23 mM.

8. The storage medium of claim 1 wherein the potassium chloride concentration is 4–6 mM.

9. The storage medium of claim 8 wherein the concentration of potassium chloride is about 5 mM.

10. The storage medium of claim 8 wherein the concentration of $NaH_2PO_4$ is 22–28 mM.

11. The storage medium of claim 10 wherein the concentration of $NaH_2PO_4$ is about 25 mM.

12. An aqueous synthetic human blood platelet storage medium consisting essentially of:
    70–120 mM sodium chloride;
    17–29 mM sodium citrate;
    3–7 mM potassium chloride; and
    1.9–3.1 calcium chloride.

13. An aqueous synthetic human blood platelet storage medium consisting essentially of:
    100–300 mEq/L sodium;
    50–300 mEq/L chloride;
    0.1–10 mEq/L potassium; and
    an amount of phosphate which is effective to maintain the pH of a unit of platelets and not more than 15 ml of associated plasma at a pH in excess of 6.6 during seven days of storage with 55 ml/unit of said medium in an oxygen permeable container maintained at from 20° to 24° C., said blood platelet storage medium being essentially free of glucose and calcium.

14. The storage medium of claim 13 wherein said medium further comprises:
    0.1–100 mEq/L of citrate.

15. The storage medium of claim 13 wherein the concentration of sodium is 140–240 mEq/L.

16. The medium of claim 15 wherein the concentration of sodium is 160–200 mEq/L.

17. The medium of claim 13 wherein the concentration of chloride is 80–150 mEq/L.

18. The medium of claim 17 wherein the concentration of chloride is 100–125 mEq/L.

19. The storage medium of claim 15 wherein the concentration of citrate is 45–75 mEq/L.

20. The storage medium of claim 19 wherein the concentration of citrate is 30–70 mEq/L.

21. The storage medium of claim 13 wherein the concentration of potassium is 2–7 mEq/L.

22. The storage medium of claim 21 wherein the concentration of potassium is about 5 mEq/L.

23. The storage medium of claim 14 wherein the concentration of magnesium is 1–4 mEq/L.

24. The storage medium of claim 23 wherein the concentration of magnesium is about 2.4 mEq/L.

25. The medium of claim 13 wherein said amount of phosphate is 5–50 mEq/L.

26. The medium of claim 25 wherein said amount of phosphate is 10–35 mEq/L.

27. The medium of claim 26 wherein said amount of phosphate is about 25 mEq/L.

28. An aqueous synthetic human blood platelet storage medium consisting essentially of:
    100–300 mEq/L of sodium;
    50–330 mEq/L of chloride;
    0.1–10 mEq/L of calcium; and
    an amount of citrate sufficient to prevent clumping of platelets during resuspension of a unit of platelets in not more then 15 ml of associated plasma when resuspended in about 55 ml/unit of said medium, said storage medium being essentially free of glucose and phosphate.

29. The invention of claim 28 wherein said amount of calcium is an amount within the range of 0.1–10 mEq/L.

30. The storage medium of claim 29 wherein the concentration of calcium is 2–7 mEq/L.

31. The storage medium of claim 30 wherein the concentration of calcium is about 5 mEq/L.

32. The storage medium of claim 28 further comprising: 0.1–6 mEq/L of magnesium;

33. The storage medium of claim 32 comprising: 1–4 mEq/L of magnesium.

34. The storage medium of claim 33 comprising about 2.4 mEq/L of magnesium.

35. The invention of claim 28 wherein the concentration of citrate is 0.1–100 mEq/L.

36. The medium of claim 28 wherein the concentration of citrate is 45–75 mEq/L.

37. The medium of claim 36 wherein the concentration of citrate is 30–70 mEq/L.

38. The storage medium of claim 28 wherein the concentration of sodium is 140–240 mEq/L.

39. The medium of claim 38 wherein the concentration of sodium is 160–200 mEq/L.

40. The medium of claim 28 wherein the concentration of chloride is 80–150 mEq/L.

41. The medium of claim 40 wherein the concentration of chloride is 100–125 mEq/L.

42. The storage medium of claim 13 further comprising:
a platelet permeable, non-glycolytic, substrate for oxidative phosphorylation.

43. The storage medium of claim 28 furthr comprising:
a platelet permeable, non-glycolytic, substrate for oxidative phosphorylation.

* * * * *